(12) United States Patent
Kamchonwongpaisan et al.

(10) Patent No.: US 11,028,072 B2
(45) Date of Patent: Jun. 8, 2021

(54) **2,4-DIAMINO-6-ETHYLPYRIMIDINE DERIVATIVES WITH ANTIMALARIAL ACTIVITIES AGAINST *PLASMODIUM FALCIPARUM***

(71) Applicant: National Science and Technology Development Agency, Pathum Thani (TH)

(72) Inventors: Sumalee Kamchonwongpaisan, Pathum Thani (TH); Netnapa Charoensetakul, Pathum Thani (TH); Krisana Peewasan, Pathum Thani (TH); Jarunee Vanichtanankul, Pathum Thani (TH); Roonglawan Rattanajak, Pathum Thani (TH); Supannee Taweechai, Pathum Thani (TH); Tosapol Anukunwithaya, Pathum Thani (TH); Aphisit Yoomuang, Pathum Thani (TH); Yongyuth Yuthavong, Pathum Thani (TH); Tirayut Vilaivan, Pathum Thani (TH)

(73) Assignee: National Science and Technology Development Agency, Pathum Thani (TH)

( * ) Notice: Subject to any disclaimer, the term of this patent is extended or adjusted under 35 U.S.C. 154(b) by 500 days.

(21) Appl. No.: 15/762,530

(22) PCT Filed: Sep. 16, 2016

(86) PCT No.: PCT/TH2016/000076
§ 371 (c)(1),
(2) Date: Mar. 22, 2018

(87) PCT Pub. No.: WO2017/052479
PCT Pub. Date: Mar. 30, 2017

(65) Prior Publication Data
US 2020/0239445 A1    Jul. 30, 2020

(30) Foreign Application Priority Data

Sep. 23, 2015  (TH) ................ 1501005737

(51) Int. Cl.
| | |
|---|---|
| *C07D 403/04* | (2006.01) |
| *C07D 413/12* | (2006.01) |
| *C07D 417/12* | (2006.01) |
| *A61P 33/06* | (2006.01) |

(52) U.S. Cl.
CPC ............ *C07D 403/04* (2013.01); *A61P 33/06* (2018.01); *C07D 413/12* (2013.01); *C07D 417/12* (2013.01)

(58) Field of Classification Search
CPC .. C07D 403/04; C07D 417/12; C07D 413/12; A61P 33/06
See application file for complete search history.

(56) References Cited

U.S. PATENT DOCUMENTS

| | | |
|---|---|---|
| 2005/0171131 A1 | 8/2005 | Kosogof et al. |
| 2015/0225353 A1 | 8/2015 | Wright et al. |

FOREIGN PATENT DOCUMENTS

| | | |
|---|---|---|
| WO | 2009/048957 A1 | 4/2009 |

OTHER PUBLICATIONS

International Search Report and Written Opinion received for PCT Patent Application No. PCT/TH2016/000076, dated Feb. 14, 2017, 8 pages.

*Primary Examiner* — Sarah Pihonak
*Assistant Examiner* — Jason Deck
(74) *Attorney, Agent, or Firm* — Morrison & Foerster LLP

(57) ABSTRACT

The present invention relates to 2,4-diamino-6-ethylpyrimidine derivatives that are inhibitors of wild type and quadruple mutant dihydrofolate reductase (DHFR) of *Plasmodium falciparum*. They also show in vitro antimalarial activities against *Plasmodium falciparum* for both wild type and mutant that are comparable to or better than pyrimethamine. In addition, the compounds of the present invention show a good selectivity to *Plasmodium falciparum* and exhibit lower cytotoxicity than pyrimethamine.

4 Claims, No Drawings

2,4-DIAMINO-6-ETHYLPYRIMIDINE DERIVATIVES WITH ANTIMALARIAL ACTIVITIES AGAINST *PLASMODIUM FALCIPARUM*

CROSS REFERENCE TO RELATED APPLICATIONS

This application is a U.S. National Phase patent application of PCT/TH2016/000076, filed Sep. 16, 2016, which claims priority to Thailand Patent Application No. 1501005737, filed Sep. 23, 2015, the disclosures of which are incorporated herein by reference in their entirety.

FIELD OF THE INVENTION

Organic chemistry and biology relates to 2,4-diamino-6-ethylpyrimidine derivatives with antimalarial activities against *Plasmodium falciparum*:

DISCLOSURE OF THE INVENTION

This invention relates to the synthesis of 2,4-diamino-6-ethylpyrimidine derivatives with a general formula (I)

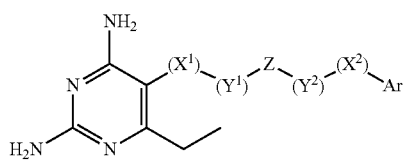

Wherein $X^1$, $X^2$ are oxygen, $Y^1$, $Y^2$ are $(CH_2)_{1-3}$ alkyl, Z is (1-substituted-1H-1,2,3-triazol-4-yl) ring, (3-(substituted)isoxazol-5-yl) ring, (2-(substituted)oxazol-4-yl) ring, (2-(substituted)thiazol-4-yl) ring, Ar is aromatic ring as described in the detailed description of the invention. $X^1$, $X^2$, $Y^1$, $Y^2$ are optionally substituted with either ones or all groups or without any group. These 2,4-diamino-6-ethylpyrimidine derivatives (I) can be developed into a drug against *Plasmodium falciparum* that is effective for drug-resistant strains, specific for *Plasmodium falciparum* and exhibit low toxicity. The compounds were tested for inhibition of the enzyme dihydrofolate reductase (DHFR) from wild type and drug resistant *Plasmodium falciparum* and also for in vitro anti-*Plasmodium falciparum* activities as well as the specificity for *Plasmodium falciparum*.

BACKGROUND OF THE INVENTION

Drug resistance in *Plasmodium falciparum* has been one of the most important problems in malaria control for a long time, and results in reducing the effectiveness and the clinical utilities of several antimalarial drugs such as pyrimethamine, trimethoprim, cycloguanil and WR99210. These drugs work by inhibition of *Plasmodium falciparum* dihydrofolate reductase (PfDHFR) that catalyzes the NADPH-dependent reduction of dihydrofolate to regenerate tetrahydrofolate, which is a cofactor required for the biosynthesis of thymidylate, which is a building block for DNA synthesis. Mechanistic studies indicated that dihydrofolate reductase enzyme can have mutations of amino acids at certain positions such as residues 16, 51, 59, 108 or 164 etc.[1,2,3] These mutations gave rise to drug resistance and thus reducing their effectiveness to pyrimethamine and cycloguanil. However, the mutation of the enzyme must have its limitation in order to get sufficient enzymatic activity for survival. For instant, some antimalaria drugs with flexible side chains, as WR99210, have been shown experimentally to cause reversion of the S108N mutation back to S108 or S108T which is sensitive or less resistant to the drugs.[4,5] The natural limitation in resistant mutation provides the opportunity to develop new effective antimalarial drugs against the current drug resistant strains.

Studies of three-dimensional structures of both wild-type and mutant pfDHFRs with antimalarial drugs that are known to inhibit DHFR such as pyrimethamine, cycloguanil, WR99210[7,8] and the new pyrimidine derivatives such as P218, provided a detailed understanding of the enzyme-inhibitor interaction at the molecular level. Hence, rational drug design of new antifolates that are effective inhibitors against antifolate resistant malaria can be performed to facilitate discovery of new effective antifolate antimalarials.

The present invention describes the rational designs and synthesis of new derivatives of 2,4-diamino-6-ethylpyrimidine which is the core structure of pyrimethamine and P218.[9] The present invention provides novel DHFR inhibitiors which are effective against both wild-type and mutant *Plasmodium falciparum* in vitro. Furthermore, the specificity towards *Plasmodium falciparum* was confirmed by testing against Human dihydrofolate reductase (hDHFR) and determination of cytotoxicity towards mammalian cells in vitro.

REFERENCE

1. Peterson, D. S. Walliker, D., Wellems, T. E., *Proc. Natl. Acad. Sci. USA*. (1988) 85, 9114-9118.
2. Foote, S. J., Galatis, D., Cowman, A. F., *Proc. Natl. Acad. Sci. USA*. (1990) 87, 3014-3017.
3. Sirawaraporn, W., Sathitkul, T., Sirawaraporn, R., Yuthavong, Y., Santi, D. V., *Proc. Natl. Acad. Sci. USA*. (1997) 94, 1124-1129.
4. Chusacultanachai, S., Thiensathit, P., Tarnchompoo, B., Sirawaraporn, W., Yuthavong, Y., *Mol. Biochem. Parasitol.* (2002) 120, 61-72.
5. Japrung, D., Leartsakulpanich, U., Chusacultanachai, S., Yuthavong, Y., *Antimicrob. Agents Chemother*. (2007) 51, 4356-4360.
6. Yuvaniyama, J., Chitnumsub, P., Kamchonwongpaisan, S., Vanichtanankul, J., Sirawaraporn, W., Taylor, P., Walkinshaw, M. D., Yuthavong, Y., *Nat. Struct. Biol.* (2003) 10, 357-365.
7. McKie, J. H., Douglas, K. T., Chan, C., Roser, S. A., Yates, R., Read, M., Hyde, J. E., Dascombe, M. J., Yothavong, Y., Sirawaraporn, W., *J. Med. Chem.* (1998) 41, 1367-1370.
8. Rastelli, G., Sirawaraporn, W., Sompornpisut, P., Vilaivan, T., Kamchonwongpaisan, S., Quarrell, R., Lowe, G., Thebtaranonth, Y., Yuthavong, Y., *Bioorg. Med. Chem.* (2000) 8, 1117-1128.
9. Yuthavong, Y., Tarnchompoo, B., Vilaivan, T., Chitnumsub, P., Kamchonwongpaisan, S., Charman, S. A., MeLennan, D. N., White, K. L., Vivas, L., Bongard, E., Thongphanchang, C., Taweechai, S., Vanichtanankul, J., Rattanajak, R., Arwon, U., Fantauzzi, P., Yuvaniyama, J., Charman, W. N., Matthews, D., *Proc. Natl. Acad. Sci. USA*. (2012) 109, 16823-16828.
10. Christian, W. T., Caspar, C., Moten, M., *J. Org. Chem.* (2002) 67, 3057-3064.
11. Hull, R., *J. Chem. Soc.* (1956), 2033-2035.

12. Tarnchompoo, B., Yothavong, Y., Vilaivan, T., Chitnumsub, P., Thongpanchang, C., Kamchonwongpaisan, S., Matthews, D., Vivas, L., Yuvaniyama, J., Charman, S., Charman, W., Katiyar, S. B., WO 2009048957 A1 (2009).
13. Lee, Y. S., Park, S. M., Kim, H. M., Park, S. K., Lee, K., Lee, C. W., Kim, B. H., *Bioorg. Med. Chem. Lett.* (2009) 19, 4688-4691.
14. Gopalakrishnan, M., Ji, J., Lee, C. H., Li, T., Sippy, K. B., WO 2009149135 A1 (2013).
15. Brown, D. R., Collins, I., Czapelwski, L. G., Hayden, D. J. WO2007107758 A1 (2007).
16. Clark, R. B., Elbaum, D. WO2007146066 A2 (2007).

DETAILED DESCRIPTION OF THE INVENTION

The present invention relates to compounds that inhibit *Plasmodium falciparum* which are derivatives of 2,4-diamino-6-ethylpyrimidine carrying substituents such as 5-(1-substituted phenyl-1H-1,2,3-triazol-4-yl), 5-(arylalkyl-1H-1,2,3-triazol-4-yl), 5-(aryl-1H-1,2,3-triazol-4-yl)alkoxy, 5-(1-aryl-1H-1,2,3-triazol-4-yl)alkoxy, 5-(3-aryl substituted isoxazol-5-yl)alkoxy, 5-(2-aryl substituted oxazol-4-yl)alkoxy and 5-(2-aryl substituted thiazol-4-yl)alkoxy (compounds of formula II, III, IV, V, VI, VII, VIII). These are new compounds developed from the core structure of pyrimethamine and P218[9] by changing substitutents at the position 5 of the pyrimidine ring of pyrimethamine and P218 to a 5-member ring heteroaromatic which one or more nitrogen, [10] sulfur or oxygen atoms. These compounds have a more flexible side-chain than pyrimethamine and exhibit additional binding interactions with amino acid side chain and hydrophobic domain between amino acid on sequence 108 to 119 including sequence 170, as arginine, of *Plasmodium falciparum*. This provides the basis for the better enzyme inhibition activities of these new inhibitors against dihydrofolate reductase of *Plasmodium falciparum* for both wild-type and quadruple mutant N51I+C59R+S108N+I1164L (mutations of the amino acids at position 51 (asparagine to isoleucine), 59 (cysteine to arginine), 108 (serine to asparagine) and 164 (isoleucine to leucine)). The antimalarial compounds of the present invention are also effective againt *P. falciparum* both wild-type and quadruple mutant in vitro. They also show selectivity for *Plasmodium falciparum* in comparison to pyrimethamine and P218. This is confirmed by determining the inhibitory activities against Human dihydrofolate reductase (hDHFR) and cytotoxicity against mammalian cells such as monkey kidney cells or vero cells.

The present invention provides compounds according to Formula I;

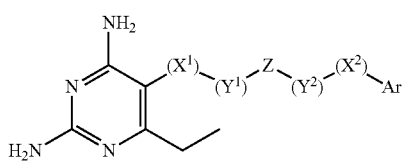

wherein
(a) $X^1$, $X^2$ are O (oxygen)
(b) $Y^1$, $Y^2$ are a 1-3 carbon alkylene chain, $(CH_2)_{1-3}$
(c) $X^1$, $X^2$, $Y^1$, $Y^2$ are optionally substituted with either ones or all groups or without any group (d) Z is a heterocyclic aromatic group such as (1-substituted-1H-1,2,3-triazol-4-yl), (3-(substituted)isoxazol-5-yl), (2-(substituted)oxazol-4-yl) or (2-(substituted)thiazol-4-yl)
(e) Ar is aromatic ring, it may be substituted at one or more available positions by phenyl, carboxyl, carboxy methyl, diphenylcarbamoyl, halogen, nitrile, nitro, hydroxyl, trifluoromethyl, alkyl, alkoxy, alkoxy carboxylate or alkoxy carbonyl-substituted phenyl;
(f) The derivative compounds of Formula (I), wherein said compound is the following compound or a pharmaceutically acceptable salt such as hydrochloride.

The compounds according to Formula (I) can be divided into 7 series. In one embodiment, Z is (1-substituted-1H-1,2,3-triazol-4-yl) as in Formula (II), (III), (IV), (V). In another embodiment, Z is (3-(substituted)isoxazol-5-yl) as in Formula (VI). In yet another embodiment, Z is (2-(substituted) oxazol-4-yl), as in Formula (VII) and in the last embodiment, Z is (2-(substituted)thiazol-4-yl) as in Formula (VIII) as shown below:

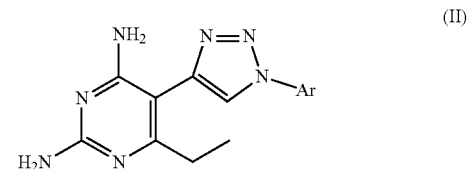

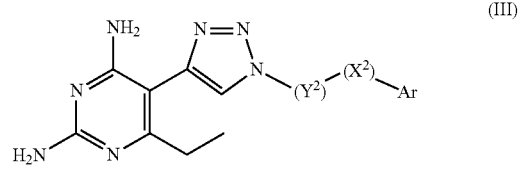

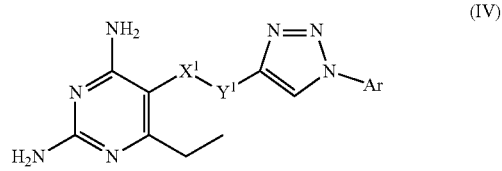

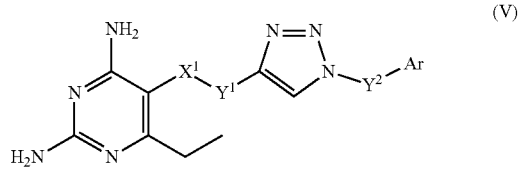

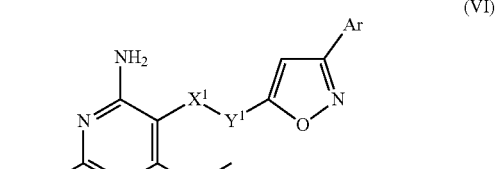

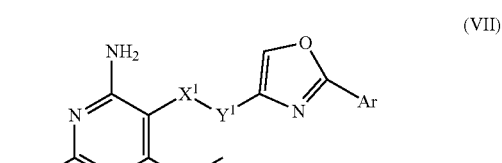

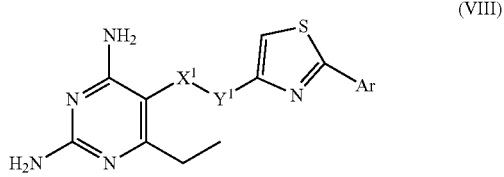

Synthesis of compounds of Formula (II) and (III) (example 1), is illustrated in Scheme 1 below.

The final step to synthesize compounds of Formula (II) and (III) involves a click reaction between 2,4-diamino-6-ethyl-5-ethynylpyrimidine (XI) and azide derivatives (XII or XIII), with copper(I) acetate or copper(II) sulfate pentahydrate/ascorbic acid as catalysts. The reaction is preferably performed in polar solvent such as acetonitrile, tert-butanol, waster etc., at room temperature to 60 degree celsius. The hydrochloride salts of the compounds of Formula (II) and (III) are readily prepared by reacting with hydrochloric acid in a suitable polar solvent.

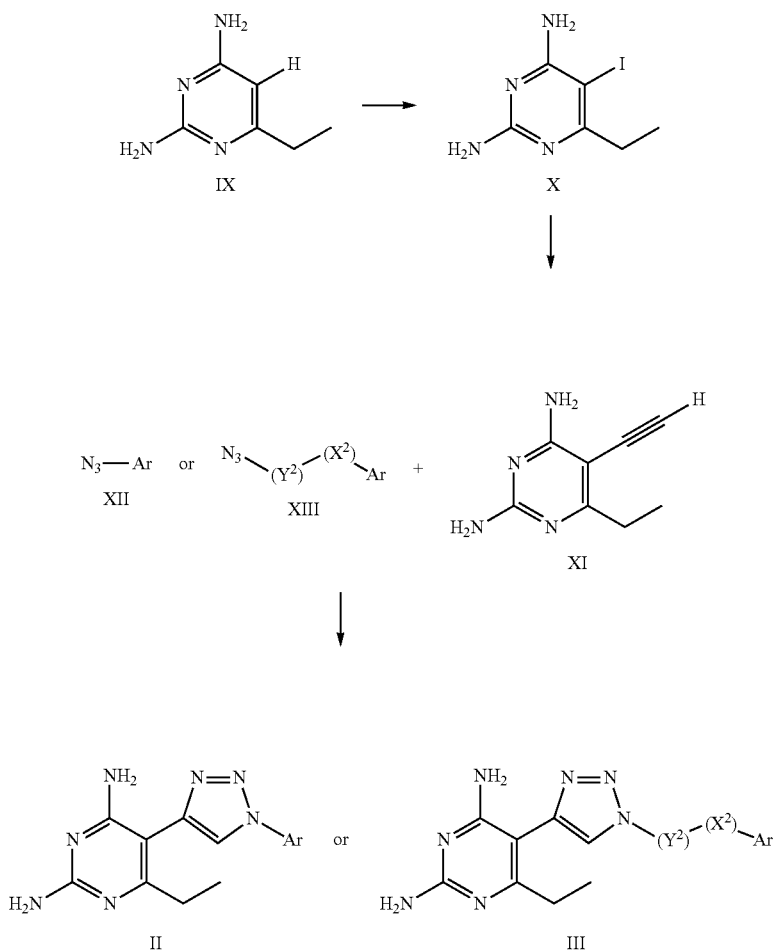

2,4-diamino-6-ethyl-5-iodopyrimidine (X) is preferably synthesized by an iodination reaction of 2,4-diamino-6-ethylpyrimidine (IX) with iodine monochloride in a polar solvent such as methanol at room temperature.

The intermediate of 2,4-diamino-6-ethyl-5-ethynylpyrimidine (XI) is synthesized from a reaction of 2,4-diamino-6-ethyl-5-iodopyrimidine (X) and ethynyltrimethylsilane in dimethyl formamide with bis-(triphenylphosphine)palladium dichloride and copper(I) iodide as catalysts under basic condition. After stirring overnight, the solvent is removed under reduced pressure and the product is purified by column chromatography. The trimethylsilyl group is removed with potassium carbonate in methanol to give the intermediate XI.

The compounds of Formula (IV)-(VIII) are prepared by alkylation of 2,4-diamino-6-ethyl-5-hydroxypyrimidine (XIV)[11] with a suitable alkyl halide in polar aprotic solvent such as N,N-dimethylformamide (DMF) under basic condition. The alkyl halides can be alkyl chlolride, alkyl bromide, alkyl iodide or alkyl sulfonate, which can be prepared by reactions known to those skilled in the arts.[12] When the substitutent of the alkyl halide is a carboxyl (—COOH) group, it is preferably protected as alkyl ester form such as an alkyl ester such as methyl or ethyl or in the form of nitrile. It is then transformed back to the carboxylic acid by hydrolysis after connection with the pyrimidine part.

Synthesis of compounds of Formula (IV) and (V) (example 2) is illustrated in Scheme 2 below.

Scheme 2

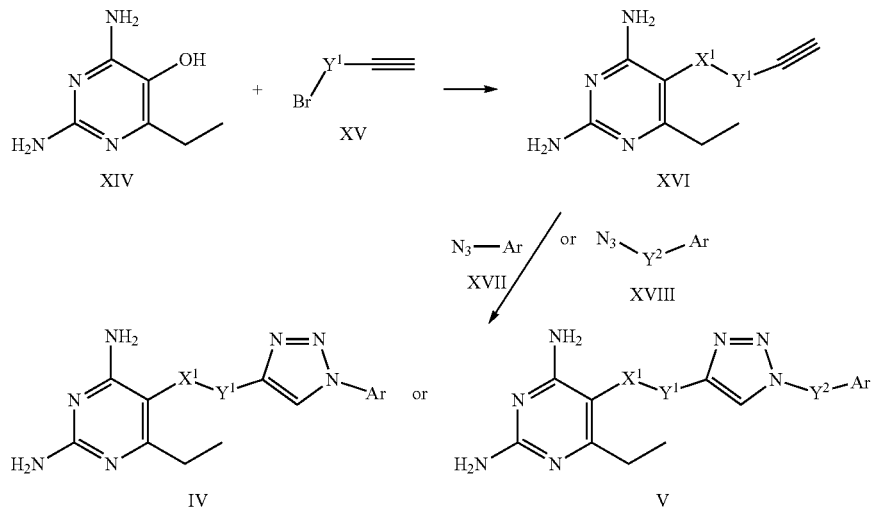

2,4-Diamino-6-ethyl-5-(prop-2-ynyloxy)pyrimidine (XVI) can be prepared by substitution reaction between 2,4-diamino-6-ethyl-5-hydroxypyrimidine (XIV) and an ethynyl alkyl halide or sulfonate such as propagyl bromide, but-3-ynyl 4-methylbenzenesulfonate or pent-4-ynyl 4-methylbenzenesulfonate in the presence of lithium hydroxide monohydrate as a base in dimethylformamide solvent. The mixture is then stirred overnight at room temperature. The product is isolated by addition of water, filtration and washing the solid with water.

The final step for synthesizing compounds of Formula (IV) and (V) involves a click reaction between pyrimidine (XVI) with azide derivatives (XVII or XVIII) in the presence of N,N-diisopropylethylamine and copper(I) acetate as catalysts in a polar solvent as acetonitrile at room temperature. Hydrochloride salts of the compounds of Formula (IV) and (V) are prepared as explained above.

Synthesis of compounds of Formula (VI) (example 3) is illustrated in Scheme 3 below.

The aldoxime compound (XX) is produced by a condensation reaction of aromatic aldehyde (XIX) and hydroxylamine hydrochloride in the presence of a base, wherein the preferred base is sodium hydroxide.[13]

The (3-substituted isoxazol-5-yl)alkyl alcohol (XXII) intermediate, can be prepared by a reaction of the aldoxime compound (XX) in polar solvent, such as methanol, dimethylformamide etc., with N-chlorosuccinimide (NCS) or bisacetoxyiodobenzene (BAIB)[14] followed by subsequent reaction with the alkyne (XXI) at room temperature for overnight. The solvent is then removed and the product is purified by column chromatography.

5-Bromoalkyl-3-substituted isoxazol intermediate (XXIII) is synthesized by bromination of the alcohol (XXII) with tetrabromomethane and triphenylphosphine in dichloromethane at room temperature. The product can be isolated and purified by conventional techniques such as evaporation and column chromatography.

Scheme 3

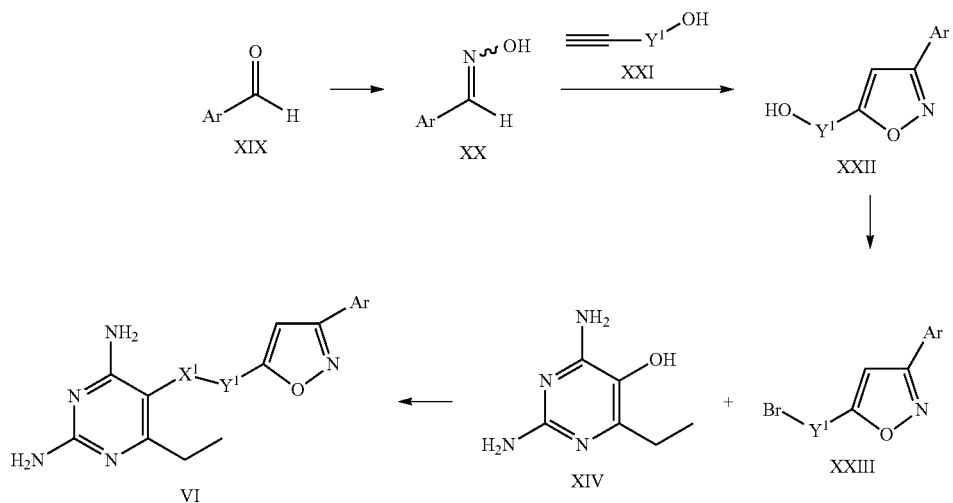

The compound of Formula (VI), as the final product, can be prepared by substitution reaction between pyrimidine (XIV) and alkyl bromide derivatives (XXIII), in the presence of lithium hydroxide monohydrate as a base and potassium iodide as a catalyst in a polar sovent, such as dimethylformamide, at room temperature. Hydrochloride salts of the compounds of Formula (VI) are readily prepared are prepared as explained above.

Synthesis of compounds of Formula (VII) and (VIII) (example 4), is illustrated in Scheme 4 below.

namely 2,4-diamino-6-ethyl-5-(1-(3-(carboxy)phenyl)-1H-1,2,3-triazol-4-yl)pyrimidine hydrochloride is provided below:

a) Synthesis of
2,4-Diamino-6-Ethyl-5-Iodopyrimidine (X) as
Intermediate

A suspension of 2,4-diamino-6-ethylpyrimidine (0.8750 g, 5.00 mmol) and iodine monochloride (0.40 mL, 7.50

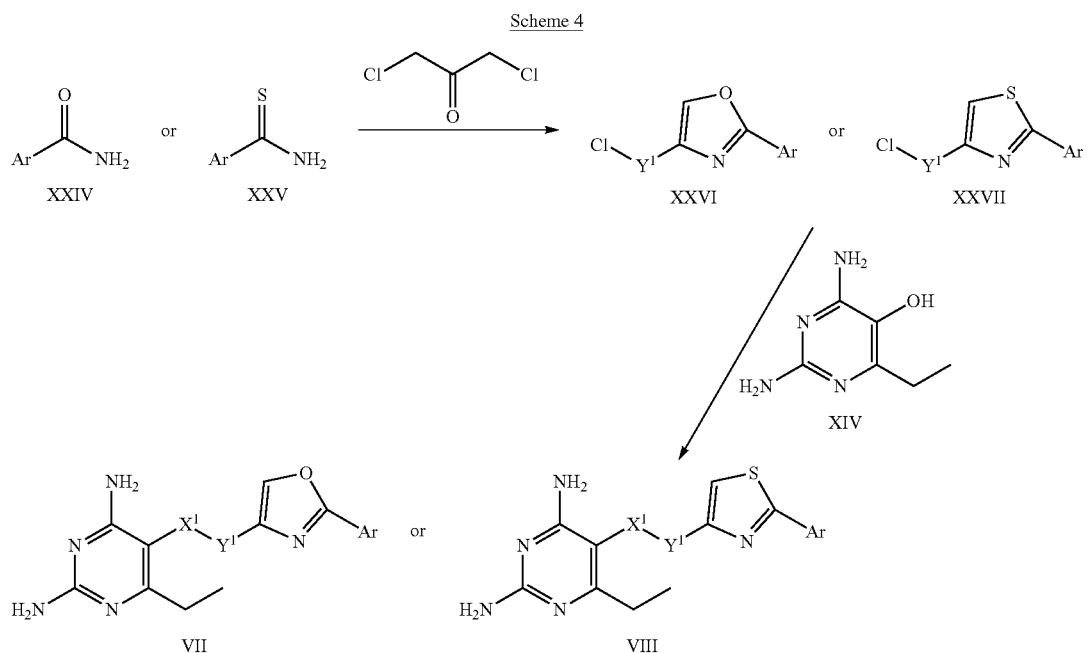

Scheme 4

4-(Chloroalkyl)-2-substituted oxazole (XXVI) or 4-(chloroalkyl)-2-substituted thiazole (XXVII) can be prepared by cyclization of aromatic amide (XXIV) or aromatic thioamide (XXV) with 1,3-dichloroacetone or ethyl 4-chloroacetoacetate[15,16] in toluene at 110 degree celsius.

In the final step, the compounds of Formula (VII) and (VIII) can be constructed by coupling reaction of the pyrimidine (XIV) and alkyl chlorides derivatives (XXVI) or (XXVII) in the presence of lithium hydroxide monohydrate as a base and potassium iodide as a catalyst in polar solvent such as dimethylformamide at room temperature. Hydrochloride salts of the compounds of (VII) and (VIII) are readily prepared are prepared as explained above.

EXAMPLES

The following examples, which disclose the preparation of representative derivative compounds of this present invention (see Table 1), are for the purpose of illustrating methods for the preparation of the 2,4-diaminopyrimidine derivatives and formulations described in this invention.

Example 1

Synthesis of 2,4-diamino-6-ethyl-5-(1-(3-(carboxy)phenyl)-1H-1,2,3-triazol-4-yl)pyrimidine Hydrochloride (Compound 2) (See Table 1)

A representative procedure for the preparation of compound of Formula (II), where Ar is 3-(caboxy)phenyl, mmol) in methanol (15 mL) was stirred at room temperature for 2 hours. Water (5 mL) was added and adjusted pH to 7 with 10% aq NaOH. The reaction was extracted 3 times with ethyl acetate (15 mL each), dried over anhydrous $MgSO_4$ and evaporated. The product was obtained as a light brown solid (1.1355 g, 86% yield).

b) Synthesis of
2,4-Diamino-6-Ethyl-5-Ethynylpyrimidine (XI) as
Intermediate

A solution of the 2,4-diamino-6-ethyl-5-iodopyrimidine (obtained in step a) (0.2640 g, 1.00 mmol) was treated with ethynyltrimethylsilane (0.40 mL, 3.00 mmol), triethylamine (0.40 mL, 3.00 mmol), bis-(triphenylphosphine)palladium dichloride [$Pd(Ph_3P)_2Cl_2$] (0.0701 g, 0.10 mmol) and copper (I) iodied (0.0381 g, 0.2 mmol) in DMF (10 mL). The reaction was stirred at 80-85° C. under nitrogen for 16 hours. After the starting material was consumed, the reaction was filtered with celite, washed with methanol and evaporated. The residue was purified by column chromatography (50% ethyl acetate in hexane as eluent) to provide a brown solid. The solid was reacted with potassium carbonate (0.1382 g, 1.00 mmol) in methanol (5 mL). The reaction mixture was filtered, washed with cold water and air-dried to give the titled as a light brown solid (0.1589 g, 98% yield).

c) Synthesis of 2,4-diamino-6-ethyl-5-(1-(3-(carboxy)phenyl)-1H-1,2,3-triazol-4-yl)pyrimidine 3-Azidobenzoic acid (0.4127 g, 2.50 mmol), copper (II) sulfate pentahydrate (0.0406 g, 0.15 mmol), ascorbic acid (0.0328 g, 0.15 mmol) and tris[(1-benzyl-1H-1,2,3-triazol-4-yl)methyl]amine (TBTA) (0.0974 g, 0.15 mmol) were added to a stirring solution of 2,4-diamino-6-ethyl-5-ethynylpyrimidine (0.2562 g, 1.50 mmol) in tert-butyl alcohol:water (2:1) (5 mL) at room temperature for overnight. The reaction mixture was evaporated and purified by column chromatography (50% ethyl acetate in hexane as eluent) to provide the yellow solid (0.2219 g, 43% yield).

d) Synthesis of 2,4-diamino-6-ethyl-5-(1-(3-(carboxy)phenyl)-1H-1,2,3-triazol-4-yl)pyrimidine Hydrochloride To a suspension of 2,4-diamino-6-ethyl-5-(1-(3-(carboxy)phenyl)-1H-1,2,3-triazol-4-yl)pyrimidine (0.1952 g, 0.60 mmol) in methanol (1 mL) was added 0.057 mL of concentrated HCl. The titled compound precipitated almost immediately and was obtained as a brown solid after suction filtration followed by washing with acetone and air-dried (0.1593 g, 73% yield).

Example 2

Synthesis of 2,4-diamino-6-ethyl-5-((1-(3-(carboxy)phenyl)-1H-1,2,3-triazol-4-yl)methoxy)pyrimidine Hydrochloride (Compound 16) (See Table 1)

a) Synthesis of 2,4-diamino-6-ethyl-5-(prop-2-ynyloxy)pyrimidine (XVI) as Intermediate A mixture of 2,4-diamino-6-ethylpyrimidine-5-ol (1.1564 g, 7.50 mmol) and propagyl bromide (0.7441 g, 5.00 mmol) in DMF (5 mL) was added lithium hydroxide monohydrate (0.8396 g, 20.00 mmol) and stirred at room temperature overnight. Water (5 mL) was added and the precipitate was collected by filtration, washed with water and air-dried. The product was obtained as a white solid (0.8361 g, 87% yield).

b) Synthesis of 2,4-diamino-6-ethyl-5-((1-(3-(carboxy)phenyl)-1H-1,2,3-triazol-4-yl)methoxy)pyrimidine To a suspension of 2,4-diamino-6-ethyl-5-(prop-2-ynyloxy)pyrimidine (0.1928 g, 1.00 mmol) and 3-azidobenzoic acid (0.3284 g, 2.00 mmol) in acetonitrile (4 mL) was added N,N-diisopropylethylamine (0.30 mL, 2.00 mmol) and copper(I) acetate (0.0191 g, 0.15 mmol) at room temperature and the reaction mixture was left stirring for 6 hours. The acetonitrile was evaporated under reduced pressure and the remaining solid was washed with saturated solution of ethylenediaminetetraacetic acid (EDTA) to provide a brown solid (0.2745 g, 77% yield).

c) Synthesis of 2,4-diamino-6-ethyl-5-((1-(3-(carboxy)phenyl)-1H-1,2,3-triazol-4-yl)methoxy)pyrimidine Hydrochloride 2,4-Diamino-6-ethyl-5-((1-(3-(carboxy)phenyl)-1H-1,2,3-triazol-4-yl)methoxy)pyrimidine (0.2487 g, 0.70 mmol) was suspended in methanol (1 mL) and one equivalent of concentrated HCl was added (0.059 mL, 0.7 mmol). Reaction mixture was stirred and left at room temperature for 30 minutes. The titled compound was obtained, after evaporation and trituration of the residue with acetone, as a brown solid (0.2118 g, 77% yield).

Example 3

Synthesis of 2,4-diamino-6-ethyl-5-(3-(3-(3-(carboxy)phenyl)isoxazol-5-yl)propoxy)pyrimidine Hydrochloride (Compound 49) (See Table 1)

a) Synthesis of 3-cyanobenzaldehyde Oxime as Intermediate

Hydroxylamine hydrochloride (1.4998 g, 21.56 mmol) was added to a stirred solution of 3-formylbenzonitirle (2.5767 g, 19.60 mmol) in water (5 mL), ethanol (5 mL) and ice (8.6 g) and the reaction mixture was stirred at 25° C. The 50% NaOH (1.97 mL, 49.00 mmol) was added into the reaction and stirred at 25° C. for 1 hour. The reaction mixture was extracted with ether to remove impurities. The aqueous layer was acidified with concentrated HCl to pH 6 (ice was added to keep the temperature at 25° C.) and then extracted again with ether. The diethyl ether phase was dried over anhydrous magnesium sulfate and evaporated to dryness. The product was obtained as a white solid (2.8701 g, 100% yield).

b) Synthesis of 3-cyano-N-hydroxybenzimidoyl Chloride as Intermediate

To a stirring solution of 3-cyanobenzaldehyde oxime (2.9153 g, 20.00 mmol) in DMF (16.60 mL) at 25° C. was added in about one-tenth portions of solid N-chlorosuccinimide (2.7012 g, 20.00 mmol). After 10 minutes, 1.40 mL of gas from the head space of a concentrated HCl reagent bottle was collected in a syringe and then was bubbled into the DMF solution. The temperature was kept below 50° C. until the reaction was completed. The reaction mixture was poured into ice water (20 mL) and extracted 2 times with ether (20 mL each). The combined diethyl ether extracts was washed 3 times with water (20 mL each) and dried over anhydrous magnesium sulfate. Upon evaporation of the diethyl ether layers gave the product as white solid (3.6001 g, 100% yield).

c) Synthesis of 3-(3-(3-cyanophenyl)isoxazol-5-yl)propanol as Intermediate

A suspension of 3-cyano-N-hydrobenzimidoyl chloride (3.3440 g, 18.50 mmol) and 4-pentyn-1-ol (1.6971 g, 19.42 mmol) in tetrahydrofuran (16 mL) was added dropwise a solution of triethylamine (3.90 mL, 27.75 mmol) in tetrahydrofuran (6 mL) and stirred at 0° C. for 2 hours or until a precipitation occurred. The tetrahydrofuran was removed by evaporation and the residue was diluted with water (20 mL). The precipitate was isolated by filtration. The water layer was extracted 3 times with ethyl acetate (15 mL each). The ethyl acetate layer was dried over anhydrous magnesium sulfate and after evaporation of solvent, the residue was purified by column chromatography (15% ethyl acetate in hexane as eluent). The titled product was obtained as light yellow liquid (1.4608 g, 34% yield).

d) Synthesis of 3-(3-(3-(carboxy)phenyl)isoxazol-5-yl)propanol as Intermediate

Sodium peroxide (0.3902 g, 5.00 mmol) was added very slowly to a solution of 3-(3-(3-cyanophenyl)isoxazol-5-yl)

propanol in water (3.5 mL) and the reaction mixture was stirred at 50° C. until the starting material was consumed. The reaction was extracted with 3 mL ether and the water layer was acidified with concentrated HCl to pH 5 and then extracted again 3 times with ether (3 mL each). The diethyl ether layer was dried over anhydrous magnesium sulfate and was evaporated. The product was obtained as a yellow solid (0.2450 g, 100% yield).

e) Synthesis of 3-(3-(3-(carboxymethyl)phenyl) isoxazol-5-yl)propanol as Intermediate To a suspension of 3-(3-(3-(carboxy)phenyl)isoxazol-5-yl)propanol (1.1100 g, 4.50 mmol) and concentrated sulfuric acid (1 mL) in absolute methanol (30 mL) was stirred at 80° C. for 8 hours. The reaction mixture was evaporated to provide the crude product, which was purified by column chromatography (25% ethyl acetate in hexane as eluent). The product was obtained as light orange liquid (0.8299 g, 71% yield).

f) Synthesis of 5-(bromopropyl)-3-(3-(carboxymethyl)phenyl)isoxazole as Intermediate A solution of 3-(3-(3-(carboxymethyl)phenyl)isoxazol-5-yl)propanol (1.0119 g, 3.90 mmol) and triphenylphosphine (1.5437 g, 5.85 mmol) in dichloromethane (22 mL) was stirred at room temperature for 2 hours. A solution of tetrabromomethane (1.9968 g, 5.85 mmol) in dichloromethane (8 mL) was added dropwise and the reaction was stirred until the starting material was consumed. Evaporation of the dichloromethane gave the crude product which was purified by column chromatography (silica gel, 6% ethyl acetate in hexane as eluent) to provide the bromo compound as light brown liquid (1.3579 g, 100% yield).

g) Synthesis of 2,4-diamino-6-ethyl-5-(3-(3-(3-(carboxymethyl)phenyl)isoxazol-5-yl) propoxy)pyrimidine Potassium iodide (0.7370 g, 4.40 mmol) and potassium carbonate (1.3860 g, 10.00 mmol) were added to a stirred solution of 2,4-diamino-6-ethylpyrimide-5-ol hyrdrochloride (0.8355 g, 4.40 mmol) and 5-(bromopropyl)-3-(3-(carboxymethyl)phenyl)isoxazole (1.3000 g, 4.00 mmol) in DMF (4 mL) and the reaction mixture was stirred at room temperature overnight. DMF was partially removed under reduced pressure to give a residue. The residue was diluted with water (10 mL) and extracted 3 times with dichloromethane (10 mL each). The combined dichloromethane layer was dried over anhydrous magnesium sulfate. Evaporation of the dichloromethane under reduced pressure gave the crude product, which was purified by column chromatography (5% MeOH in CH$_2$Cl$_2$ as eluent) to obtain title compound as a white solid (0.6015 g, 37% yield).

h) Synthesis of 2,4-diamino-6-ethyl-5-(3-(3-(3-(carboxy)phenyl)isoxazol-5-yl)propoxy)pyrimidine 2,4-Diamino-6-ethyl-5-(3-(3-(3-(carboxymethyl)phenyl) isoxazol-5-yl)propoxy)pyrimidine (0.2370 g, 0.60 mmol) was added to a stirred solution of 2 M sodium hydroxide (0.40 mL, 0.72 mmol) and the reaction mixture was heated at 100° C. with stirring until the starting material has been consumed. The reaction was acidified with 2 M HCl (0.70 mL, 1.32 mmol). The titled compound precipitated and solid was collected by filtration and washed with 10% solution of HCl, acetone and air-dried. The product was obtained as white solid (0.1827 g, 80% yield).

i) Synthesis of 2,4-diamino-6-ethyl-5-(3-(3-(3-(carboxy)phenyl)isoxazol-5-yl)propoxy)pyrimidine Hydrochloride To a stirring suspension of 2,4-diamino-6-ethyl-5-(3-(3-(3-(carboxy)phenyl) isoxazol-5-yl)propoxy)pyrimidine (0.1601 g, 0.417 mmol) in methanol (1 mL) was added one equivalent of concentrated hydrochloric acid (0.036 mL, 0.417 mmol) at room temperature. After evaporation of solvent and trituration with acetone, product was obtained as yellow solid (0.1709 g, 97% yield).

Example 4

Synthesis of 2,4-diamino-6-ethyl-5-((2-(3-(carboxy) phenyl)thiazol-4-yl)methoxy)pyrimidine Hydrochloride (Compound 66) (See Table 1)

a) Synthesis of 4-(chloromethyl)-2-(3-(carboxymethyl)phenyl)thiazole as Intermediate A mixture of methyl 3-carbamothioylbenzoate (1.9504 g, 9.99 mmol) and 1,3-dichloroacetone (2.5449 g, 19.98 mmol) in toluene (10 mL) was stirred at 110° C. for 6 hours. The toluene was partially removed under reduced pressure to give residue. The residue was purified by column chromatography, eluting with 5% ethyl acetate in hexane. The product was obtained as a white solid (2.1007 g, 78% yield).

b) Synthesis of 2,4-diamino-6-ethyl-5-((2-(3-(carboxymethyl)phenyl)thiazol-4-yl)methoxy)pyrimidine Potassium iodide (0.5493 g, 3.30 mmol) and potassium carbonate (1.0536 g, 7.50 mmol) were added to a stirred solution of 2,4-diamino-6-ethylpyrimidine-5-ol hydrochloride (0.6292 g, 3.30 mmol) and 4-(chloromethyl)-2-(3-(carboxymethyl)phenyl)thiazole (0.8081 g, 3.00 mmol) in DMF (3 mL) and the reaction mixture was stirred at room temperature overnight. Some DMF was removed under reduced pressure to give a residue, which was diluted with water (10 mL) and extracted 3 times with dichloromethane (10 mL each). The combined dichloromethane layer was dried over anhydrous magnesium sulfate. Evaporation of the dichloromethane under reduced pressure gave the crude product, which was purified by column chromatography (1% MeOH in CH$_2$Cl$_2$ as eluent). The desired diaminopyrimidine was obtained as a yellow solid (0.5153 g, 44% yield).

c) Synthesis of 2,4-diamino-6-ethyl-5-((2-(3-(carboxy)phenyl)thiazol-4-yl)methoxy)pyrimidine Hydrochloride To a suspension of 2,4-diamino-6-ethyl-5-((2-(3-(carboxymethyl)phenyl)thiazol-4-yl)methoxy)pyrimidine (0.1972 g, 0.51 mmol) in water (0.50 mL) was added five equivalents of concentrated HCl (0.01 mL, 2.5 mmol) and the reaction mixture was heated to reflux at 110° C. and stirred until the starting material disappeared. Cooling at room temperature of the reaction mixture resulted in precipitation of the product, which was collected by filtration and washed with acetone. The hydrochloride salt was obtained as yellow solid (0.1090 g, 52% yield).

Example 5

In accordance with the procedure of Example 1, 2, 3 and 4 described above, the following 2,4-diaminopyrimidine derivatives of Formula (II), (III), (IV), (V), (VI), (VII) and (VIII) can be prepared in the form of hydrochloride salt as derivatives (1)-(76) shown in Table 1. Their $^1$H NMR spectra are summarized in Table 2 below.

TABLE 1

2,4-Diamino-6-ethylpyrimidine derivatives

| Cmpd. | Formula | $X^1$ | $Y^1$ | $Y^2$ | $X^2$ | Ar | Melting Point (° C.) |
|---|---|---|---|---|---|---|---|
| 1 | II | — | — | — | — | Ph | 273.2-274.5 |
| 2 | II | — | — | — | — | 3-(HOOC)$C_6H_4$ | 205.0-207.0 |
| 3 | III | — | — | $CH_2$ | — | Ph | 255.5-256.5 |
| 4 | III | — | — | $CH_2$ | — | 4-($CH_3$OOC)$C_6H_4$ | 222.0-223.0 |
| 5 | III | — | — | $CH_2$ | — | 4-(HOOC)$C_6H_4$ | 270.0-272.0 |
| 6 | III | — | — | $CH_2$ | — | 4-($Ph_2$NCOO)$C_6H_4$ | 138.0-139.0 |
| 7 | III | — | — | $(CH_2)_2$ | — | Ph | 203.0-204.5 |
| 8 | III | — | — | $(CH_2)_3$ | — | Ph | 233.0-235.0 |
| 9 | III | — | — | $(CH_2)_2$ | O | 4-(Cl)$C_6H_4$ | 173.5-175.0 |
| 10 | III | — | — | $(CH_2)_2$ | O | 4-($CH_3$OOC)$C_6H_4$ | 225.0-226.0 |
| 11 | III | — | — | $(CH_2)_3$ | O | 4-(Cl)$C_6H_4$ | 222.5-223.5 |
| 12 | III | — | — | $(CH_2)_3$ | O | 4-($CH_3$OOC)$C_6H_4$ | 211.0-212.0 |
| 13 | IV | O | $CH_2$ | — | — | Ph | 212.5-213.5 |
| 14 | IV | O | $CH_2$ | — | — | 3-($NO_2$)$C_6H_4$ | 236.0-237.0 |
| 15 | IV | O | $CH_2$ | — | — | 3-($CH_3$OOC)$C_6H_4$ | 211.0-212.0 |
| 16 | IV | O | $CH_2$ | — | — | 3-(HOOC)$C_6H_4$ | 197.5-199.5 |
| 17 | IV | O | $CH_2$ | — | — | 4-($NO_2$)$C_6H_4$ | 209.0-210.5 |
| 18 | IV | O | $CH_2$ | — | — | 4-($CH_3$OOC)$C_6H_4$ | 197.5-199.0 |
| 19 | IV | O | $CH_2$ | — | — | 4-(HOOC)$C_6H_4$ | 270.8-272.0 |
| 20 | IV | O | $(CH_2)_2$ | — | — | 3-(HOOC)$C_6H_4$ | 246.0-247.0 |
| 21 | IV | O | $(CH_2)_2$ | — | — | 4-($CH_3$OOC)$C_6H_4$ | 190.0-192.0 |
| 22 | IV | O | $(CH_2)_2$ | — | — | 4-(HOOC)$C_6H_4$ | 270.0-271.0 |
| 23 | IV | O | $(CH_2)_3$ | — | — | 3-(HOOC)$C_6H_4$ | 230.5-231.5 |
| 24 | IV | O | $(CH_2)_3$ | — | — | 4-($CH_3$OOC)$C_6H_4$ | 208.0-209.5 |
| 25 | IV | O | $(CH_2)_3$ | — | — | 4-(HOOC)$C_6H_4$ | 239.5-241.5 |
| 26 | V | O | $CH_2$ | $CH_2$ | — | 3-(HOOC)$C_6H_4$ | 170.0-171.0 |
| 27 | V | O | $CH_2$ | $CH_2$ | — | 3,5-($F_2$)-4-(OH)$C_6H_2$ | 224.7-226.0 |
| 28 | V | O | $CH_2$ | $CH_2$ | — | 4-(OH)$C_6H_4$ | 224.2-225.2 |
| 29 | V | O | $CH_2$ | $CH_2$ | — | 4-(HOOC)$C_6H_4$ | 223.8-224.8 |
| 30 | V | O | $(CH_2)_2$ | $CH_2$ | — | 4-(OH)$C_6H_4$ | 213.0-215.0 |
| 31 | V | O | $(CH_2)_3$ | $CH_2$ | — | 3-(HOOC)$C_6H_4$ | 222.5-223.5 |
| 32 | V | O | $(CH_2)_3$ | $CH_2$ | — | 4-(HOOC)$C_6H_4$ | 211.0-212.5 |
| 33 | VI | O | $CH_2$ | — | — | Ph | 221.5-222.5 |
| 34 | VI | O | $CH_2$ | — | — | 4-(F)$C_6H_4$ | 231.0-232.0 |
| 35 | VI | O | $CH_2$ | — | — | 4-(Cl)$C_6H_4$ | 230.0-231.5 |
| 36 | VI | O | $CH_2$ | — | — | 4-(Br)$C_6H_4$ | 238.0-239.5 |
| 37 | VI | O | $CH_2$ | — | — | 3-($CF_3$)$C_6H_4$ | 224.0-225.5 |
| 38 | VI | O | $CH_2$ | — | — | 3-($CH_3$O)$C_6H_4$ | 211.5-212.5 |
| 39 | VI | O | $CH_2$ | — | — | 3-($NO_2$)$C_6H_4$ | 179.5-181.5 |
| 40 | VI | O | $CH_2$ | — | — | 3-(HOOC)$C_6H_4$ | 192.0-194.0 |
| 41 | VI | O | $CH_2$ | — | — | 4-($CF_3$)$C_6H_4$ | 173.0-174.5 |
| 42 | VI | O | $CH_2$ | — | — | 4-($CH_3$O)$C_6H_4$ | 214.0-216.0 |
| 43 | VI | O | $CH_2$ | — | — | 4-($NO_2$)$C_6H_4$ | 216.0-218.0 |
| 44 | VI | O | $CH_2$ | — | — | 4-(HOOC)$C_6H_4$ | 242.0-244.0 |
| 45 | VI | O | $(CH_2)_3$ | — | — | 4-(Cl)$C_6H_4$ | 231.5-232.5 |
| 46 | VI | O | $(CH_2)_3$ | — | — | 3-($CF_3$)$C_6H_4$ | 216.5-218.0 |
| 47 | VI | O | $(CH_2)_3$ | — | — | 3-(CN)$C_6H_4$ | 252.0-253.0 |
| 48 | VI | O | $(CH_2)_3$ | — | — | 3-($CH_3$OOC)$C_6H_4$ | 188.0-189.5 |
| 49 | VI | O | $(CH_2)_3$ | — | — | 3-(HOOC)$C_6H_4$ | 219.0-220.5 |
| 50 | VII | O | $CH_2$ | — | — | Ph | 231.0-232.0 |
| 51 | VII | O | $CH_2$ | — | — | 3-($CH_3$)$C_6H_4$ | 225.0-226.0 |
| 52 | VII | O | $CH_2$ | — | — | 3-($NO_2$)$C_6H_4$ | 221.5-222.5 |
| 53 | VII | O | $CH_2$ | — | — | 3-(PhCH$_2$OOCCH$_2$O)$C_6H_4$ | 163.5-164.5 |
| 54 | VII | O | $CH_2$ | — | — | 3-(HOOCCH$_2$O)$C_6H_4$ | 203.0-204.0 |
| 55 | VII | O | $CH_2$ | — | — | 4-(Cl)$C_6H_4$ | 239.0-240.0 |
| 56 | VII | O | $CH_2$ | — | — | 4-(PhCH$_2$OOCCH$_2$O)$C_6H_4$ | 191.5-192.5 |
| 57 | VII | O | $CH_2$ | — | — | 4-(HOOCCH$_2$O)$C_6H_4$ | 195.5-197.5 |
| 58 | VII | O | $(CH_2)_2$ | — | — | Ph | 254.5-255.5 |
| 59 | VII | O | $(CH_2)_2$ | — | — | 4-(HOOC)$C_6H_4$ | 330.0-332.0 |
| 60 | VIII | O | $CH_2$ | — | — | Ph | 220.0-222.0 |

TABLE 1-continued 2,4-Diamino-6-ethylpyrimidine derivatives

| Cmpd. | Formula | X¹ | Y¹ | Y² | X² | Ar | Melting Point (° C.) |
|---|---|---|---|---|---|---|---|
| 61 | VIII | O | $CH_2$ | — | — | 3-$(CH_3)C_6H_4$ | 232.0-233.0 |
| 62 | VIII | O | $CH_2$ | — | — | 3-$(NO_2)C_6H_4$ | 235.0-236.5 |
| 63 | VIII | O | $CH_2$ | — | — | 3-$(PhCH_2OOCCH_2O)C_6H_4$ | 175.0-177.0 |
| 64 | VIII | O | $CH_2$ | — | — | 3-$(HOOCCH_2O)C_6H_4$ | 191.0-193.0 |
| 65 | VIII | O | $CH_2$ | — | — | 3-$(CH_3OOC)C_6H_4$ | 224.5-226.5 |
| 66 | VIII | O | $CH_2$ | — | — | 3-$(HOOC)C_6H_4$ | 217.5-219.0 |
| 67 | VIII | O | $CH_2$ | — | — | 4-$(CH_3)C_6H_4$ | 235.0-236.0 |
| 68 | VIII | O | $CH_2$ | — | — | 4-$(CH_3O)C_6H_4$ | 228.0-229.0 |
| 69 | VIII | O | $CH_2$ | — | — | 4-$(F)C_6H_4$ | 226.0-227.0 |
| 70 | VIII | O | $CH_2$ | — | — | 4-$(Cl)C_6H_4$ | 230.0-232.0 |
| 71 | VIII | O | $CH_2$ | — | — | 4-$(Br)C_6H_4$ | 236.0-238.0 |
| 72 | VIII | O | $CH_2$ | — | — | 4-$(PhCH_2OOCCH_2O)C_6H_4$ | 178.0-180.0 |
| 73 | VIII | O | $CH_2$ | — | — | 4-$(HOOCCH_2O)C_6H_4$ | 203.5-205.5 |
| 74 | VIII | O | $CH_2$ | — | — | 4-$(CH_3OOC)C_6H_4$ | 217.0-219.0 |
| 75 | VIII | O | $CH_2$ | — | — | 4-$(HOOC)C_6H_4$ | 213.0-214.0 |
| 76 | VIII | O | $(CH_2)_2$ | — | — | Ph | 215.0-217.0 |

TABLE 2

¹H NMR spectra of 2,4-diamino-6-ethylpyrimidine derivatives

| Cmpd. | ¹H NMR (in DMSO $d_6$, 400 MHz) |
|---|---|
| 1 | 1.17 (3H, $CH_3$, t, J = 6.9 Hz), 2.43 (2H, $CH_2$, q, J = 7.1 Hz), 7.40-7.56 (3H, CH-Aromatic, m), 7.60-7.68 (2H, CH-Aromatic, t, J = 7.3 Hz), 7.80 (1H, NH, brs), 7.96 (2H, 2xNH, brs), 8.32 (1H, NH, brs), 8.98 (1H, CH, s), 13.20 (1H, NH, brs) |
| 2 | 1.11 (3H, $CH_3$, t, J = 7.5 Hz), 2.38 (2H, $CH_2$, q, J = 7.5 Hz), 6.77 (2H, 2xNH, brs), 6.93 (2H, 2xNH, brs), 7.75 (1H, CH-Aromatic, t, J = 7.9 Hz), 8.06 (1H, CH-Aromatic, d, J = 7.8 Hz), 8.20 (1H, CH-Aromatic, d, J = 8.0 Hz), 8.49 (1H, CH-Aromatic, s), 8.94 (1H, CH, s) |
| 3 | 1.13 (3H, $CH_3$, t, J = 7.5 Hz), 2.38 (2H, $CH_2$, q, J = 7.5 Hz), 5.67 (2H, $CH_2$, s), 7.32-7.43 (5H, CH-Aromatic, m), 7.48 (1H, NH, brs), 7.71 (2H, 2xNH, brs), 8.32 (1H, NH, brs), 8.40 (1H, CH, s), 12.87 (1H, NH, brs) |
| 4 | 1.15 (3H, $CH_3$, t, J = 7.5 Hz), 2.39 (2H, $CH_2$, q, J = 7.5 Hz), 3.86 (3H, $CH_3O$, s), 5.79 (1H, $CH_2$, s), 7.50 (2H, CH-Aromatic, d, J = 8.2 Hz), 7.50 (1H, NH, brs), 7.78 (2H, 2xNH, brs), 7.98 (2H, CH-Aromatic, d, J = 8.2 Hz), 8.34 (1H, NH, brs), 8.45 (1H, CH, s), 13.14 (1H, NH, brs) |
| 5 | 1.12 (3H, $CH_3$, t, J = 7.5 Hz), 2.37 (2H, $CH_2$, q, J = 7.4 Hz), 5.76 (2H, $CH_2$, s), 7.45 (2H, CH-Aromatic, d, J = 8.3 Hz), 7.55 (2H, 2xNH, brs), 7.95 (2H, CH-Aromatic, d, J = 8.3 Hz), 8.39 (1H, CH, s), 12.90 (1H, OH, brs) |
| 6 | 1.09 (3H, $CH_3$, t, J = 7.5 Hz), 2.35 (2H, $CH_2$, q, J = 7.4 Hz), 5.65 (2H, $CH_2$, s), 7.20-7.30 (5H, CH-Aromatic, m), 7.36-7.62 (9H, CH-Aromatic, m), 7.36-7.62 (3H, 3xNH, brs), 8.30 (1H, NH, brs), 8.39 (1H, CH, s), 12.42 (1H, NH, brs) |
| 7 | 1.08 (3H, $CH_3$, t, J = 7.2 Hz), 2.27 (2H, $CH_2$, q, J = 7.2 Hz), 3.22 (2H, $CH_2$, t, J = 6.4 Hz), 4.68 (2H, $CH_2$, t, J = 6.5 Hz), 7.14-7.34 (5H, CH-Aromatic, m), 7.34 (1H, NH, brs), 7.73 (2H, 2xNH, brs), 8.14 (1H, CH, s), 8.30 (1H, NH, brs), 13.04 (1H, NH, brs) |
| 8 | 1.12 (3H, $CH_3$, t, J = 7.5 Hz), 2.18 (2H, $CH_2$, m), 2.37 (2H, $CH_2$, q, J = 7.4 Hz), 2.61 (2H, $CH_2$, t, J = 7.6 Hz), 4.39 (2H, $CH_2$, t, J = 7.0 Hz), 7.12-7.22 (3H, CH-Aromatic, m), 7.24-7.32 (2H, CH-Aromatic, m), 7.66 (2H, 2xNH, brs), 8.16 (1H, NH, brs), 8.30 (1H, CH, s), 13.09 (1H, NH, brs) |
| 9 | 1.11 (3H, $CH_3$, t, J = 7.5 Hz), 2.36 (2H, $CH_2$, q, J = 7.5 Hz), 4.47 (2H, $CH_2$, t, J = 4.9 Hz), 4.82 (2H, $CH_2O$, t, J = 4.9 Hz), 6.96 (2H, CH-Aromatic, d, J = 8.8 Hz), 7.33 (2H, CH-Aromatic, d, J = 8.8 Hz), 7.38 (1H, NH, brs), 7.69 (2H, 2xNH, brs), 8.26 (1H, NH, brs), 8.35 (1H, CH, s), 12.98 (1H, NH, brs) |
| 10 | 1.11 (3H, $CH_3$, t, J = 7.5 Hz), 2.36 (2H, $CH_2$, q, J = 7.5 Hz), 3.81 (3H, $CH_3O$, s), 4.56 (2H, $CH_2$, t, J = 4.9 Hz), 4.86 (2H, $CH_2O$, t, J = 4.9 Hz), 7.05 (2H, CH-Aromatic, d, J = 8.6 Hz), 7.39 (1H, NH, brs), 7.76 (2H, 2xNH, brs), 7.90 (2H, CH-Aromatic, d, J = 8.6 Hz), 8.30 (1H, NH, brs), 8.37 (1H, CH, s), 13.08 (1H, NH, brs) |
| 11 | 1.08 (3H, $CH_3$, t, J = 7.5 Hz), 2.33 (4H, 2x$CH_2$, m), 4.01 (2H, $CH_2$, t, J = 6.7 Hz), 4.56 (2H, $CH_2O$, t, J = 6.7 Hz), 6.93 (2H, CH-Aromatic, d, 8.8 Hz), 7.30 (2H, CH-Aromatic, d, J = 8.8 Hz), 7.64 (2H, 2xNH, brs), 8.17 (2H, 2xNH, brs), 8.29 (1H, CH, s), 13.01 (1H, NH, brs) |
| 12 | 1.09 (3H, $CH_3$, t, J = 7.5 Hz), 2.38 (4H, 2x$CH_2$, m), 3.82 (3H, $CH_3O$, s), 4.15 (2H, $CH_2$, t, J = 6.0 Hz), 4.60 (2H, $CH_2O$, t, J = 6.7 Hz), 7.05 (2H, CH-Aromatic, d, J = 8.6 Hz), 7.46 (3H, 3xNH, brs), 7.92 (2H, CH-Aromatic, d, J = 8.6 Hz), 8.24 (1H, NH, brs), 8.31 (1H, CH, s), 12.40 (1H, NH, brs) |

TABLE 2-continued

<sup>1</sup>H NMR spectra of 2,4-diamino-6-ethylpyrimidine derivatives

| Cmpd. | $^1$H NMR (in DMSO $d_6$, 400 MHz) |
|---|---|
| 13 | 1.07 (3H, CH$_3$, t, J = 7.5 Hz), 2.44 (2H, CH$_2$, q, J = 7.5 Hz), 5.01 (2H, CH$_2$O, s), 7.54 (1H, CH-Aromatic, d, J = 7.5 Hz), 7.53 (2H, 2xNH, brs), 7.63 (2H, CH-Aromatic, t, J = 7.8 Hz), 7.91 (2H, CH-Aromatic, d, J = 7.6 Hz), 8.04 (1H, NH, brs), 8.44 (1H, NH, brs), 8.99 (1H, CH, s), 12.65 (1H, NH, brs) |
| 14 | 1.08 (3H, CH$_3$, t, J = 7.5 Hz), 2.45 (2H, CH$_2$, q, J = 7.5 Hz), 5.02 (2H, CH$_2$O, s), 7.56 (2H, 2xNH, brs), 7.93 (1H, CH-Aromatic, t, J = 8.2 Hz), 8.00 (1H, NH, brs), 8.36 (1H, CH-Aromatic, dd, J = 1.6, 8.2 Hz), 8.42 (1H, CH-Aromatic, m), 8.43 (1H, NH, brs), 8.72 (1H, CH-Aromatic, s), 9.20 (1H, CH, s), 12.60 (1H, NH, brs) |
| 15 | 1.07 (3H, CH$_3$, t, J = 7.5 Hz), 2.44 (2H, CH$_2$, q, J = 7.5 Hz), 3.93 (3H, CH$_3$O, s), 5.01 (2H, CH$_2$O, s), 7.44 (2H, 2xNH, brs), 7.80 (1H, CH-Aromatic, t, J = 7.9 Hz), 8.08 (1H, CH-Aromatic, d, J = 7.8 Hz), 8.08 (1H, NH, brs), 8.21 (1H, CH-Aromatic, d, J = 8.0 Hz), 8.21 (1H, NH, brs), 8.42 (1H, CH-Aromatic, s), 9.10 (1H, CH, s), 12.42 (1H, NH, brs) |
| 16 | 1.08 (3H, CH$_3$, t, J = 7.2 Hz), 2.45 (2H, CH$_2$, q, J = 7.2 Hz), 5.00 (2H, CH$_2$O, s), 7.63 (2H, 2xNH, brs), 7.74 (1H, CH-Aromatic, t, J = 7.8 Hz), 8.05 (1H, CH-Aromatic, d, J = 7.7 Hz), 8.05 (1H, NH, brs), 8.15 (1H, CH-Aromatic, d, J = 7.8 Hz), 8.15 (1H, NH, brs), 8.39 (1H, CH-Aromatic, s), 9.09 (1H, CH, s) |
| 17 | 1.08 (3H, CH$_3$, t, J = 7.6 Hz), 2.45 (2H, CH$_2$, q, J = 7.6 Hz), 5.02 (2H, CH$_2$O, s), 7.56 (2H, 2xNH, brs), 8.00 (1H, NH, brs), 8.24 (2H, CH-Aromatic, d, J = 9.1 Hz), 8.42 (1H, NH, brs), 8.48 (2H, CH-Aromatic, d, J = 9.1 Hz), 9.18 (1H, CH, s), 12.65 (1H, NH, brs) |
| 18 | 1.08 (3H, CH$_3$, t, J = 7.5 Hz), 2.45 (2H, CH$_2$, q, J = 7.5 Hz), 3.91 (3H, CH$_3$O, s), 5.01 (2H, CH$_2$O, s), 7.54 (2H, 2xNH, brs), 7.98 (1H, NH, brs), 8.10 (2H, CH-Aromatic, d, J = 8.7 Hz), 8.19 (2H, CH-Aromatic, d, J = 8.7 Hz), 8.41 (1H, NH, brs), 9.09 (1H, CH, s), 12.59 (1H, NH, brs) |
| 19 | 1.06 (3H, CH$_3$, t, J = 7.5 Hz), 2.44 (2H, CH$_2$, q, J = 7.5 Hz), 5.00 (2H, CH$_2$O, s), 7.54 (2H, 2xNH, brs), 8.00 (1H, NH, brs), 8.04 (2H, CH-Aromatic, d, 8.5 Hz), 8.15 (2H, CH-Aromatic, d, J = 8.5 Hz), 8.40 (1H, NH, brs), 9.06 (1H, CH, s) |
| 20 | 1.14 (3H, CH$_3$, m), 2.50 (2H, CH$_2$, m), 3.23 (2H, CH$_2$, m), 4.11 (2H, CH$_2$O, m), 7.24 (1H, NH, brs), 7.43 (1H, NH, brs), 7.50 (2H, 2xNH, brs), 7.75 (1H, CH-Aromatic, m), 8.04 (1H, CH-Aromatic, d, J = 5.8 Hz), 8.16 (1H, CH-Aromatic, d, J = 4.1 Hz), 8.40 (1H, CH, s), 8.40 (1H, NH, brs), 8.85 (1H, CH-Aromatic, s), 12.71 (1H, OH, brs) |
| 21 | 1.04 (3H, CH$_3$, t, J = 7.5 Hz), 2.37 (2H, CH$_2$, q, J = 7.3 Hz), 3.18 (2H, CH$_2$, t, J = 6.3 Hz), 3.87 (3H, CH$_3$, s), 4.02 (2H, CH$_2$O, t, 6.2 Hz), 6.75 (2H, 2xNH, brs), 7.48 (2H, 2xNH, brs), 8.06 (2H, CH-aromatic, d, J = 8.7 Hz), 8.15 (2H, CH-aromatic, d, J = 8.8 Hz), 8.83 (1H, CH, s) |
| 22 | 1.12 (3H, CH$_3$, t, J = 7.5 Hz), 2.46 (2H, CH$_2$, q, J = 7.5 Hz), 3.23 (2H, CH$_2$, t, J = 6.0 Hz), 4.10 (2H, CH$_2$O, t, J = 6.0 Hz), 7.45 (2H, 2xNH, brs), 8.05 (2H, CH-Aromatic, d, J = 8.6 Hz), 8.15 (2H, CH-Aromatic, d, J = 8.6 Hz), 8.15 (1H, NH, brs), 8.41 (1H, NH, brs), 8.82 (1H, CH, s), 12.41 (1H, OH, brs) |
| 23 | 1.20 (3H, CH$_3$, t, J = 7.0 Hz), 2.16 (2H, CH$_2$, m), 2.58 (2H, CH$_2$, q, J = 7.1 Hz), 2.89 (2H, CH$_2$, t, J = 6.5 Hz), 3.81 (2H, CH$_2$O, t, J = 5.0 Hz), 7.52 (2H, 2xNH, brs), 7.74 (1H, CH-Aromatic, t, J = 7.8 Hz), 7.91 (1H, NH, brs), 8.03 (1H, CH-Aromatic, d, J = 7.6 Hz), 8.15 (1H, CH-Aromatic, d, J = 7.8 Hz), 8.35 (1H, NH, brs), 8.40 (1H, CH-Aromatic, s), 8.80 (1H, CH, s), 12.80 (1H, OH, brs) |
| 24 | 1.17 (3H, CH$_3$, m), 2.16 (2H, CH$_2$, m), 2.55 (2H, CH$_2$, m), 2.90 (2H, CH$_2$, t, J = 6.9 Hz), 3.80 (2H, CH$_2$O, t, J = 5.5 Hz), 3.90 (3H, CH$_3$O, s), 7.16 (2H, 2xNH, brs), 7.84 (2H, 2xNH, brs), 8.07 (2H, CH-Aromatic, d, J = 8.2 Hz), 8.16 (2H, CH-Aromatic, d, J = 8.2 Hz), 8.78 (1H, CH, s) |
| 25 | 1.18 (3H, CH$_3$, t, J = 7.4 Hz), 2.16 (2H, CH$_2$, m), 2.57 (2H, CH$_2$, q, J = 7.4 Hz), 2.90 (2H, CH$_2$, t, J = 7.1 Hz), 3.81 (2H, CH$_2$O, t, J = 6.0 Hz), 7.42 (2H, 2xNH, brs), 7.91 (1H, NH, brs), 8.04 (2H, CH-Aromatic, d, J = 8.1 Hz), 8.14 (2H, CH-Aromatic, d, J = 8.2 Hz), 8.29 (1H, NH, brs), 8.77 (1H, CH, s), 12.51 (1H, OH, brs) |
| 26 | 1.02 (3H, CH$_3$, t, J = 7.0 Hz), 2.34 (2H, CH$_2$, q, J = 7.2 Hz), 4.90 (2H, CH$_2$, s), 5.73 (2H, CH$_2$O, s), 7.32 (1H, NH, brs), 7.39 (1H, NH, brs), 7.53 (2H, CH-Aromatic, m), 7.91 (2H, CH-Aromatic, m), 8.00 (1H, NH, brs), 8.35 (1H, CH, s), 8.37 (1H, NH, brs), 12.49 (1H, OH, brs) |
| 27 | 1.01 (3H, CH$_3$, t, J = 7.5 Hz), 2.34 (2H, CH$_2$, q, J = 7.5 Hz), 4.89 (2H, CH$_2$, s), 5.53 (2H, CH$_2$O, s), 7.08 (2H, CH-Aromatic, d, J = 7.8 Hz), 7.45 (2H, 2xNH, brs), 8.00 (1H, NH, brs), 8.30 (1H, CH, s), 8.38 (1H, NH, brs), 10.38 (1H, NH, brs), 12.32 (1H, OH, brs) |
| 28 | 1.01 (3H, CH$_3$, t, J = 7.4 Hz), 2.32 (2H, CH$_2$, q, J = 7.4 Hz), 4.87 (2H, CH$_2$, s), 5.48 (2H, CH$_2$O, s), 6.77 (2H, CH-Aromatic, d, J = 8.0 Hz), 7.17 (2H, CH-Aromatic, d, J = 8.0 Hz), 7.45 (2H, 2xNH, brs), 7.99 (1H, NH, brs), 8.21 (1H, CH, s), 8.37 (1H, NH, brs), 9.59 (1H, NH, brs), 12.32 (1H, OH, brs) |
| 29 | 1.05 (3H, CH$_3$, t, J = 6.0 Hz), 2.37 (2H, CH$_2$, q, J = 6.7 Hz), 4.92 (2H, CH$_2$, s), 5.74 (2H, CH$_2$O, s), 7.39 (2H, CH-Aromatic, d, J = 6.9 Hz), 7.55 (2H, 2xNH, brs), 7.96 (2H, CH-Aromatic, d, J = 6.8 Hz), 7.96 (1H, NH, brs), 8.35 (1H, CH, s), 8.35 (1H, NH, brs), 12.72 (1H, NH, brs), 12.72 (1H, OH, brs) |
| 30$^a$ | 1.08 (3H, CH$_3$, t, J = 7.6 Hz), 2.39 (2H, CH$_2$, q, J = 7.6 Hz), 3.14 (2H, CH$_2$, t, J = 5.8 Hz), 4.08 (2H, CH$_2$O, t, J = 5.8 Hz), 5.45 (2H, CH$_2$, s), 6.77 (2H, CH-Aromatic, d, J = 8.3 Hz), 7.21 (2H, CH-Aromatic, d, J = 8.3 Hz), 7.78 (1H, CH, s) |
| 31 | 1.17 (3H, CH$_3$, t, J = 7.4 Hz), 2.16 (2H, CH$_2$, m), 2.56 (2H, CH$_2$, q, J = 7.4 Hz), 2.89 (2H, CH$_2$, t, J = 7.3 Hz), 3.51 (2H, CH$_2$, s), 3.80 (2H, CH$_2$O, t, J = 6.3 Hz), 7.41 (2H, 2xNH, brs), 7.73 (1H, CH-Aromatic, t, J = 7.9 Hz), 7.97 (1H, NH, brs), 8.03 (1H, CH-Aromatic, d, J = 7.8 Hz), 8.14 (1H, CH-Aromatic, dd, J = 1.3, 8.0 Hz), 8.40 (1H, CH-Aromatic, s), 8.79 (1H, CH, s) |

TABLE 2-continued $^1$H NMR spectra of 2,4-diamino-6-ethylpyrimidine derivatives

| Cmpd. | $^1$H NMR (in DMSO $d_6$, 400 MHz) |
|---|---|
| 32 | 1.11 (3H, CH$_3$, t, J = 7.5 Hz), 2.07 (2H, CH$_2$, m), 2.54 (2H, CH$_2$, q, J = 7.5 Hz), 2.80 (2H, CH$_2$, t, J = 7.1 Hz), 3.75 (2H, CH$_2$O, t, J = 6.1 Hz), 5.67 (2H, CH$_2$, s), 7.23 (2H, 2xNH, brs), 7.37 (2H, CH-Aromatic, d, J = 8.0 Hz), 7.94 (2H, CH-Aromatic, d, J = 8.0 Hz), 7.97 (1H, NH, brs), 8.01 (1H, CH, s), 8.35 (1H, NH, brs), 11.65 (1H, NH, brs), 13.01 (1H, OH, brs) |
| 33 | 1.12 (3H, CH$_3$, t, J = 7.6 Hz), 2.44 (2H, CH$_2$, q, J = 7.6 Hz), 5.04 (2H, CH$_2$O, s), 7.24 (1H, CH, s), 7.53 (3H, CH-Aromatic, m), 7.61 (2H, 2xNH, brs), 7.89 (2H, CH-Aromatic, m), 8.09 (1H, NH, brs), 8.43 (1H, NH, brs), 12.71 (1H, NH, brs) |
| 34 | 1.12 (3H, CH$_3$, t, J = 7.6 Hz), 2.45 (2H, CH$_2$, q, J = 7.6 Hz), 5.04 (2H, CH$_2$O, s), 7.24 (1H, CH, s), 7.38 (2H, CH-Aromatic, t, J = 8.8 Hz), 7.56 (2H, 2xNH, brs), 7.96 (2H, CH-Aromatic, dd, J = 5.5, 8.7 Hz), 8.07 (1H, NH, brs), 8.42 (1H, NH, brs), 12.60 (1H, NH, brs) |
| 35 | 1.12 (3H, CH$_3$, t, J = 7.6 Hz), 2.44 (2H, CH$_2$, q, J = 7.6 Hz), 5.04 (2H, CH$_2$O, s), 7.27 (1H, CH, s), 7.56 (2H, 2xNH, brs), 7.61 (2H, CH-Aromatic, d, J = 8.5 Hz), 7.92 (2H, CH-Aromatic, d, J = 8.5 Hz), 8.11 (1H, NH, brs), 8.40 (1H, NH, brs), 12.69 (1H, NH, brs) |
| 36 | 1.12 (3H, CH$_3$, t, J = 7.6 Hz), 2.45 (2H, CH$_2$, q, J = 7.6 Hz), 5.04 (2H, CH$_2$O, s), 7.26 (1H, CH, s), 7.56 (2H, 2xNH, brs), 7.75 (2H, CH-Aromatic, d, J = 8.5 Hz), 7.86 (2H, CH-Aromatic, d, J = 8.5 Hz), 8.07 (1H, NH, brs), 8.41 (1H, NH, brs), 12.61 (1H, NH, brs) |
| 37 | 1.13 (3H, CH$_3$, t, J = 7.6 Hz), 2.45 (2H, CH$_2$, q, J = 7.6 Hz), 5.07 (2H, CH$_2$O, s), 7.42 (1H, CH, s), 7.59 (2H, 2xNH, brs), 7.80 (1H, CH-Aromatic, t, J = 7.7 Hz), 7.91 (1H, CH-Aromatic, d, J = 7.8 Hz), 8.09 (1H, NH, brs), 8.23 (2H, CH-Aromatic, d, J = 8.6 Hz), 8.43 (1H, NH, brs), 12.66 (1H, NH, brs) |
| 38 | 1.12 (3H, CH$_3$, t, J = 7.6 Hz), 2.44 (2H, CH$_2$, q, J = 7.6 Hz), 3.84 (3H, CH$_3$O, s), 5.04 (2H, CH$_2$O, s), 7.10 (1H, CH-Aromatic, td, J = 2.5, 6.4 Hz), 7.25 (1H, CH, s), 7.42 (1H, CH-Aromatic, dd, J = 2.0, 3.7 Hz), 7.46 (2H, CH-Aromatic, d, J = 6.4 Hz), 7.56 (2H, 2xNH, brs), 8.08 (1H, NH, brs), 8.40 (1H, NH, brs), 12.61 (1H, NH, brs) |
| 39 | 1.13 (3H, CH$_3$, t, J = 7.6 Hz), 2.46 (2H, CH$_2$, q, J = 7.6 Hz), 5.08 (2H, CH$_2$O, s), 7.47 (1H, CH, s), 7.59 (2H, 2xNH, brs), 7.86 (1H, CH-Aromatic, t, J = 8.0 Hz), 8.08 (1H, NH, brs), 8.37 (2H, CH-Aromatic, m), 8.43 (1H, NH, brs), 8.67 (1H, CH-Aromatic, s), 12.65 (1H, NH, brs) |
| 40 | 1.13 (3H, CH$_3$, t, J = 7.6 Hz), 2.45 (2H, CH$_2$, q, J = 7.6 Hz), 5.05 (2H, CH$_2$O, s), 7.35 (1H, CH, s), 7.62 (2H, 2xNH, brs), 7.68 (1H, CH-Aromatic, t, J = 7.7 Hz), 8.08 (1H, CH-Aromatic, d, J = 7.7 Hz), 8.10 (1H, NH, brs), 8.14 (1H, CH-Aromatic, d, J = 7.7 Hz), 8.42 (1H, CH-Aromatic, s), 8.44 (1H, NH, brs), 12.78 (1H, NH, brs), 13.30 (1H, OH, brs) |
| 41 | 1.12 (3H, CH$_3$, t, J = 7.6 Hz), 2.45 (2H, CH$_2$, q, J = 7.6 Hz), 5.07 (2H, CH$_2$O, s), 7.36 (1H, CH, s), 7.58 (2H, 2xNH, brs), 7.91 (2H, CH-Aromatic, d, J = 8.3 Hz), 8.13 (2H, CH-Aromatic, d, J = 8.2 Hz), 8.37 (2H, 2xNH, brs), 12.73 (1H, NH, brs) |
| 42 | 1.12 (3H, CH$_3$, t, J = 7.3 Hz), 2.44 (2H, CH$_2$, q, J = 6.9 Hz), 3.93 (3H, CH$_3$O, s), 5.03 (2H, CH$_2$O, s), 7.25 (1H, CH, s), 7.30 (2H, CH-Aromatic, d, J = 8.5 Hz), 7.57 (1H, NH, brs), 7.86 (2H, CH-Aromatic, d, J = 8.5 Hz), 7.95 (1H, NH, brs), 8.07 (1H, NH, brs), 8.42 (1H, NH, brs), 12.57 (1H, NH, brs) |
| 43 | 1.13 (3H, CH$_3$, t, J = 7.6 Hz), 2.46 (2H, CH$_2$, q, J = 7.6 Hz), 5.08 (2H, CH$_2$O, s), 7.41 (1H, CH, s), 7.55 (2H, 2xNH, brs), 8.10 (1H, NH, brs), 8.19 (2H, CH-Aromatic, d, J = 8.9 Hz), 8.39 (2H, CH-Aromatic, d, J = 8.9 Hz), 8.39 (1H, NH, brs), 12.61 (1H, NH, brs) |
| 44 | 1.12 (3H, CH$_3$, t, J = 7.6 Hz), 2.44 (2H, CH$_2$, q, J = 7.6 Hz), 5.05 (2H, CH$_2$O, s), 7.32 (1H, CH, s), 7.52 (2H, 2xNH, brs), 8.01 (1H, NH, brs), 8.02 (2H, CH-Aromatic, d, J = 8.4 Hz), 8.04 (1H, NH, brs), 8.08 (2H, CH-Aromatic, d, J = 8.4 Hz), 8.14 (1H, NH, brs), 12.98 (1H, OH, brs) |
| 45 | 1.19 (3H, CH$_3$, t, J = 7.6 Hz), 2.18 (2H, CH$_2$, m), 2.56 (2H, CH$_2$, q, J = 7.6 Hz), 2.98 (2H, CH$_2$, t, J = 7.5 Hz), 3.80 (2H, CH$_2$O, t, J = 6.3 Hz), 6.92 (1H, CH, s), 7.50 (2H, 2xNH, brs), 7.59 (2H, CH-Aromatic, d, J = 8.5 Hz), 7.85 (1H, NH, brs), 7.88 (2H, CH-Aromatic, d, J = 8.5 Hz), 8.34 (1H, NH, brs), 12.62 (1H, NH, brs) |
| 46 | 1.16 (3H, CH$_3$, t, J = 7.6 Hz), 2.19 (2H, CH$_2$, m), 2.56 (2H, CH$_2$, q, J = 7.6 Hz), 3.01 (2H, CH$_2$, t, J = 7.5 Hz), 3.82 (2H, CH$_2$O, t, J = 6.3 Hz), 7.08 (1H, CH, s), 7.28 (2H, 2xNH, brs), 7.78 (1H, CH-Aromatic, t, J = 7.7 Hz), 7.89 (1H, CH-Aromatic, d, J = 7.7 Hz), 7.89 (1H, NH, brs), 8.18 (2H, CH-Aromatic, d, J = 9.2 Hz), 8.31 (1H, NH, brs), 11.87 (1H, NH, brs) |
| 47 | 1.19 (3H, CH$_3$, t, J = 7.5 Hz), 2.19 (2H, CH$_2$, m), 2.57 (2H, CH$_2$, q, J = 7.5 Hz), 3.01 (2H, CH$_2$, t, J = 7.5 Hz), 3.82 (2H, CH$_2$O, t, J = 6.3 Hz), 7.03 (1H, CH, s), 7.44 (2H, 2xNH, brs), 7.74 (1H, CH-Aromatic, t, J = 7.8 Hz), 7.84 (1H, NH, brs), 7.99 (1H, CH-Aromatic, d, J = 7.7 Hz), 8.21 (1H, CH-Aromatic, d, J = 7.9 Hz), 8.32 (2H, CH-Aromatic, s), 8.32 (1H, NH, brs), 12.41 (1H, NH, brs) |
| 48 | 1.19 (3H, CH$_3$, t, J = 7.6 Hz), 2.20 (2H, CH$_2$, m), 2.57 (2H, CH$_2$, q, J = 7.6 Hz), 3.00 (2H, CH$_2$, t, J = 7.5 Hz), 3.81 (2H, CH$_2$O, t, J = 6.3 Hz), 3.91 (3H, CH$_3$O, s), 7.01 (1H, CH, s), 7.44 (2H, 2xNH, brs), 7.70 (1H, CH-Aromatic, t, J = 7.8 Hz), 7.84 (1H, NH, brs), 8.08 (1H, CH-Aromatic, d, J = 7.8 Hz), 8.13 (1H, CH-Aromatic, d, J = 7.8 Hz), 8.33 (1H, NH, brs), 8.40 (1H, CH-Aromatic, s), 12.43 (1H, NH, brs) |
| 49 | 1.19 (3H, CH$_3$, t, J = 7.6 Hz), 2.20 (2H, CH$_2$, m), 2.57 (2H, CH$_2$, q, J = 7.6 Hz), 3.00 (2H, CH$_2$, t, J = 7.4 Hz), 3.81 (2H, CH$_2$O, t, J = 6.3 Hz), 7.00 (1H, CH, s), 7.43 (2H, 2xNH, brs), 7.66 (1H, CH-Aromatic, t, J = 7.8 Hz), 7.85 (1H, NH, brs), 8.06 (1H, CH-Aromatic, d, J = 7.8 Hz), 8.10 (1H, CH-Aromatic, d, J = 7.8 Hz), 8.33 (1H, NH, brs), 8.39 (1H, CH-Aromatic, s), 12.37 (1H, OH, brs) |

TABLE 2-continued

<sup>1</sup>H NMR spectra of 2,4-diamino-6-ethylpyrimidine derivatives

| Cmpd. | $^1$H NMR (in DMSO $d_6$, 400 MHz) |
|---|---|
| 50 | 1.10 (3H, CH$_3$, t, J = 7.6 Hz), 2.52 (2H, CH$_2$, q, J = 7.6 Hz), 4.84 (2H, CH$_2$O, s), 7.53-7.58 (3H, CH-Aromatic, m), 7.61 (1H, NH, brs), 7.99 (2H, CH-Aromatic, m), 8.09 (1H, NH, brs), 8.31 (1H, CH, s), 8.45 (1H, NH, brs), 12.76 (1H, NH, brs) |
| 51 | 1.10 (3H, CH$_3$, t, J = 7.6 Hz), 2.48-2.56 (5H, CH$_2$ and CH$_3$, m), 4.84 (2H, CH$_2$O, s), 7.38 (1H, CH-Aromatic, d, J = 7.6 Hz), 7.45 (1H, CH-Aromatic, t, 7.6 Hz), 7.53 (2H, 2xNH, brs), 7.79 (1H, CH-Aromatic, d, J = 7.8 Hz), 7.82 (1H, CH-Aromatic, s), 8.08 (1H, NH, brs), 8.29 (1H, CH, s), 8.44 (1H, NH, brs), 12.58 (1H, NH, brs) |
| 52 | 1.11 (3H, CH$_3$, t, J = 7.6 Hz), 2.55 (2H, CH$_2$, q, J = 7.6 Hz), 4.86 (2H, CH$_2$O, s), 7.58 (2H, 2xNH, brs), 7.88 (1H, CH-Aromatic, t, J = 8.0 Hz), 8.01 (1H, NH, brs), 8.39 (1H, CH-Aromatic, d, J = 2.2 Hz), 8.41 (1H, CH-Aromatic, d, J = 1.2 Hz), 8.43 (1H, CH, s), 8.44 (1H, NH, brs), 8.67 (1H, CH-Aromatic, s), 12.70 (1H, NH, brs) |
| 53 | 1.07 (3H, CH$_3$, t, J = 7.5 Hz), 2.51 (2H, CH$_2$, m), 4.82 (2H, CH$_2$O, s), 5.01 (2H, CH$_2$O, s), 5.22 (2H, CH$_2$O, s), 7.13 (2H, 2xNH, brs), 7.16 (1H, CH-Aromatic, dd, J = 2.2, 8.2 Hz), 7.30-7.40 (5H, CH-Aromatic, m), 7.47 (1H, CH-Aromatic, s), 7.50 (1H, CH-Aromatic, d, J = 8.1 Hz), 7.61 (1H, CH-Aromatic, d, J = 7.7 Hz), 7.98 (2H, 2xNH, brs), 8.30 (1H, CH, s), 12.06 (1H, NH, brs) |
| 54 | 1.10 (3H, CH$_3$, t, J = 7.5 Hz), 2.55 (2H, CH$_2$, q, J = 7.5 Hz), 4.80 (2H, CH$_2$O, s), 4.84 (2H, CH$_2$O, s), 7.13 (1H, CH-Aromatic, dd, J = 2.3, 7.9 Hz), 7.45 (1H, CH-Aromatic, s), 7.49 (1H, CH-Aromatic, J = 8.0 Hz), 7.50 (2H, 2xNH, brs), 7.60 (1H, CH-Aromatic, d, J = 7.8 Hz), 8.07 (1H, NH, brs), 8.31 (1H, CH, s), 8.44 (1H, NH, brs), 12.49 (1H, OH, brs) |
| 55 | 1.10 (3H, CH$_3$, t, J = 7.6 Hz), 2.54 (2H, CH$_2$, q, J = 7.6 Hz), 4.84 (2H, CH$_2$O, s), 7.54 (2H, 2xNH, brs), 7.64 (2H, CH-Aromatic, d, J = 8.5 Hz), 8.00 (2H, CH-Aromatic, d, J = 8.5 Hz), 8.03 (1H, NH, brs), 8.33 (1H, CH, s), 8.42 (1H, NH, brs), 12.61 (1H, NH, brs) |
| 56 | 1.09 (3H, CH$_3$, t, J = 7.5 Hz), 2.55 (2H, CH$_2$, q, J = 7.5 Hz), 4.82 (2H, CH$_2$O, s), 4.99 (2H, CH$_2$O, s), 5.22 (2H, CH$_2$O, s), 7.12 (2H, CH-Aromatic, d, J = 8.9 Hz), 7.36-7.40 (5H, CH-Aromatic, m), 7.50 (2H, 2xNH, brs), 7.92 (2H, CH-Aromatic, d, J = 8.9 Hz), 8.09 (1H, NH, brs), 8.24 (1H, CH, s), 8.43 (1H, NH, brs), 12.47 (1H, NH, brs) |
| 57 | 1.10 (3H, CH$_3$, t, J = 7.6 Hz), 2.54 (2H, CH$_2$, q, J = 7.6 Hz), 4.79 (2H, CH$_2$O, s), 4.82 (2H, CH$_2$O, s), 7.09 (2H, CH-Aromatic, d, J = 8.9 Hz), 7.56 (2H, 2xNH, brs), 7.92 (2H, CH-Aromatic, d, J = 8.9 Hz), 8.09 (1H, NH, brs), 8.23 (1H, CH, s), 8.43 (1H, NH, brs), 12.66 (1H, OH, brs) |
| 58 | 1.12 (3H, CH$_3$, t, J = 7.6 Hz), 2.51 (2H, CH$_2$, q, J = 5.6 Hz), 3.03 (2H, CH$_2$, t, J = 6.1 Hz), 4.05 (2H, CH$_2$O, t, J = 6.2 Hz), 7.46 (2H, 2xNH, brs), 7.55 (3H, CH-Aromatic, m), 7.97 (2H, CH-Aromatic, m), 8.04 (1H, NH, brs), 8.07 (1H, CH, s), 8.42 (1H, NH, brs), 12.53 (1H, NH, brs) |
| 59 | 1.09 (3H, CH$_3$, t, J = 7.5 Hz), 2.45 (2H, CH$_2$, q, J = 7.5 Hz), 3.04 (2H, CH$_2$, t, J = 6.1 Hz), 4.02 (2H, CH$_2$O, t, J = 6.2 Hz), 6.88 (2H, 2xNH, brs), 7.52 (2H, 2xNH, brs), 8.06 (2H, CH-Aromatic, d, J = 8.8 Hz), 8.09 (2H, CH-Aromatic, d, J = 8.8 Hz), 8.14 (1H, CH, s) |
| 60 | 1.13 (3H, CH$_3$, t, J = 7.6 Hz), 2.53 (2H, CH$_2$, q, J = 7.2 Hz), 4.97 (2H, CH$_2$O, s), 7.53 (3H, CH-Aromatic, m), 7.61 (2H, 2xNH, brs), 7.85 (1H, CH, s), 7.94 (2H, CH-Aromatic, m), 8.25 (1H, NH, brs), 8.52 (1H, NH, brs), 12.78 (1H, NH, brs) |
| 61 | 1.12 (3H, CH$_3$, t, J = 7.6 Hz), 2.41 (3H, CH$_3$, s), 2.54 (2H, CH$_2$, q, J = 7.6 Hz), 4.97 (2H, CH$_2$O, s), 7.34 (1H, CH-Aromatic, d, J = 7.5 Hz), 7.42 (1H, CH-Aromatic, t, J = 7.5 Hz), 7.52 (2H, 2xNH, brs), 7.74 (2H, CH-Aromatic, d, J = 8.4 Hz), 7.83 (1H, CH, s), 8.25 (1H, NH, brs), 8.52 (1H, NH, brs), 12.56 (1H, NH, brs) |
| 62 | 1.13 (3H, CH$_3$, t, J = 7.6 Hz), 2.54 (2H, CH$_2$, q, J = 7.6 Hz), 5.01 (2H, CH$_2$O, s), 7.58 (2H, 2xNH, brs), 7.83 (1H, CH-Aromatic, t, J = 8.0 Hz), 7.99 (1H, CH, s), 8.10 (1H, NH, brs), 8.35 (2H, CH-Aromatic, t, J = 7.9 Hz), 8.47 (1H, NH, brs), 8.67 (1H, CH-Aromatic, s), 12.72 (1H, NH, brs) |
| 63 | 1.11 (3H, CH$_3$, t, J = 7.6 Hz), 2.55 (2H, CH$_2$, q, J = 7.6 Hz), 4.97 (2H, CH$_2$O, s), 5.00 (2H, CH$_2$O, s), 5.22 (2H, CH$_2$O, s), 7.12 (1H, CH-Aromatic, dd, J = 2.1, 8.1 Hz), 7.30-7.39 (5H, CH-Aromatic, m), 7.40-7.53 (2H, CH-aromatic, m), 7.47 (2H, 2xNH, brs), 7.56 (1H, CH-Aromatic, d, J = 7.8 Hz), 7.86 (1H, CH, s), 8.20 (1H, NH, brs), 8.49 (1H, NH, brs), 12.36 (1H, NH, brs) |
| 64 | 1.13 (3H, CH$_3$, t, J = 7.6 Hz), 2.56 (2H, CH$_2$, q, J = 7.6 Hz), 4.80 (2H, CH$_2$O, s), 4.97 (2H, CH$_2$O, s), 7.09 (1H, CH-Aromatic, dd, J = 2.1, 8.1 Hz), 7.42 (1H, CH-Aromatic, t, J = 2.4 Hz), 7.46 (1H, CH-Aromatic, d, J = 8.1 Hz), 7.50 (2H, 2xNH, brs), 7.54 (1H, CH-Aromatic, d, J = 7.8 Hz), 7.85 (1H, CH, s), 8.18 (1H, NH, brs), 8.48 (1H, NH, brs), 12.50 (1H, OH, brs) |
| 65 | 1.11 (3H, CH$_3$, t, J = 7.5 Hz), 2.54 (2H, CH$_2$, m), 3.92 (3H, CH$_3$O, s), 4.98 (2H, CH$_2$O, s), 7.24 (2H, 2xNH, brs), 7.70 (1H, CH-Aromatic, t, J = 7.7 Hz), 7.91 (1H, CH, s), 8.04 (2H, 2xNH, brs), 8.09 (1H, CH-aromatic, d, J = 7.7 Hz), 8.21 (1H, CH-Aromatic, d, J = 7.7 Hz), 8.49 (1H, CH-Aromatic, s), 12.38 (1H, NH, brs) |
| 66 | 1.12 (3H, CH$_3$, t, J = 7.6 Hz), 2.55 (2H, CH$_2$, q, J = 7.6 Hz), 4.99 (2H, CH$_2$O, s), 7.56 (2H, 2xNH, brs), 7.67 (1H, CH-Aromatic, t, J = 7.8 Hz), 7.91 (1H, CH, s), 8.06 (1H, CH-Aromatic, d, J = 7.8 Hz), 8.12 (1H, NH, brs), 8.18 (1H, CH-Aromatic, d, J = 7.9 Hz), 8.47 (1H, CH-Aromatic, s), 8.47 (1H, NH, brs), 12.70 (1H, OH, brs) |
| 67 | 1.12 (3H, CH$_3$, t, J = 7.6 Hz), 2.37 (3H, CH$_3$, s), 2.54 (2H, CH$_2$, q, J = 7.6 Hz), 4.96 (2H, CH$_2$O, s), 7.34 (2H, CH-Aromatic, d, J = 8.1 Hz), 7.55 (2H, 2xNH, brs), 7.80 (1H, CH, s), 7.83 (2H, CH-Aromatic, d, J = 8.1 Hz), 8.26 (1H, NH, brs), 8.51 (1H, NH, brs), 12.63 (1H, NH, brs) |

TABLE 2-continued $^1$H NMR spectra of 2,4-diamino-6-ethylpyrimidine derivatives

| Cmpd. | $^1$H NMR (in DMSO $d_6$, 400 MHz) |
|---|---|
| 68 | 1.12 (3H, CH$_3$, t, J = 7.6 Hz), 2.55 (2H, CH$_2$, q, J = 7.6 Hz), 3.84 (3H, CH$_3$O, s), 4.95 (2H, CH$_2$O, s), 7.08 (2H, CH-Aromatic, d, J = 8.8 Hz), 7.52 (2H, 2xNH, brs), 7.74 (1H, CH, s), 7.88 (2H, CH-Aromatic, d, J = 8.8 Hz), 8.28 (1H, NH, brs), 8.50 (1H, NH, brs), 12.55 (1H, NH, brs) |
| 69 | 1.12 (3H, CH$_3$, t, J = 7.6 Hz), 2.54 (2H, CH$_2$, q, J = 7.6 Hz), 4.96 (2H, CH$_2$O, s), 7.37 (2H, CH-Aromatic, t, J = 8.7 Hz), 7.53 (2H, 2xNH, brs), 7.85 (1H, CH, s), 8.00 (2H, CH-Aromatic, dd, J = 5.3, 8.7 Hz), 8.20 (1H, NH, brs), 8.48 (1H, NH, brs), 12.61 (1H, NH, brs) |
| 70 | 1.11 (3H, CH$_3$, t, J = 7.6 Hz), 2.53 (2H, CH$_2$, q, J = 7.7 Hz), 4.97 (2H, CH$_2$O, s), 7.49 (2H, 2xNH, brs), 7.60 (2H, CH-Aromatic, d, J = 8.5 Hz), 7.88 (1H, CH, s), 7.96 (2H, CH-Aromatic, d, J = 8.5 Hz), 8.26 (2H, 2xNH, brs), 12.59 (1H, NH, brs) |
| 71 | 1.11 (3H, CH$_3$, t, J = 7.6 Hz), 2.53 (2H, CH$_2$, q, J = 7.6 Hz), 4.97 (2H, CH$_2$O, s), 7.53 (2H, 2xNH, brs), 7.73 (2H, CH-Aromatic, d, J = 8.5 Hz), 7.89 (1H, CH, s), 7.89 (2H, CH-Aromatic, d, J = 8.4 Hz), 8.17 (1H, NH, brs), 8.47 (1H, NH, brs), 12.58 (1H, NH, brs) |
| 72 | 1.12 (3H, CH$_3$, t, J = 7.6 Hz), 2.55 (2H, CH$_2$, q, J = 7.6 Hz), 4.94 (2H, CH$_2$O, s), 4.99 (2H, CH$_2$O, s), 5.22 (2H, CH$_2$O, s), 7.08 (2H, CH-Aromatic, d, J = 8.8 Hz), 7.31-7.40 (5H, CH-Aromatic, m), 7.44 (2H, 2xNH, brs), 7.76 (1H, CH, s), 7.87 (2H, CH-Aromatic, d, J = 8.8 Hz), 8.30 (2H, 2xNH, brs), 12.52 (1H, NH, brs) |
| 73 | 1.13 (3H, CH$_3$, t, J = 7.6 Hz), 2.55 (2H, CH$_2$, q, J = 7.6 Hz), 4.79 (2H, CH$_2$O, s), 4.94 (2H, CH$_2$O, s), 7.05 (2H, CH-Aromatic, d, J = 8.8 Hz), 7.57 (2H, 2xNH, brs), 7.76 (1H, CH, s), 7.87 (2H, CH-Aromatic, d, J = 8.8 Hz), 8.27 (1H, NH, brs), 8.50 (1H, NH, brs), 12.70 (1H, OH, brs) |
| 74 | 1.11 (3H, CH$_3$, t, J = 7.6 Hz), 2.53 (2H, CH$_2$, q, J = 7.6 Hz), 3.90 (3H, CH$_3$O, s), 5.00 (2H, CH$_2$O, s), 7.52 (2H, 2xNH, brs), 7.96 (1H, CH, s), 8.09 (4H, CH-Aromatic, s), 8.18 (1H, NH, brs), 8.48 (1H, NH, brs), 12.53 (1H, NH, brs) |
| 75 | 1.12 (3H, CH$_3$, t, J = 7.6 Hz), 2.51 (2H, CH$_2$, m), 4.97 (2H, CH$_2$O, s), 7.28 (2H, 2xNH, brs), 7.94 (1H, CH, s), 8.00 (2H, 2xNH, brs), 8.07 (4H, CH-Aromatic, m) |
| 76 | 1.05 (3H, CH$_3$, t, J = 7.5 Hz), 2.41 (2H, CH$_2$, q, J = 7.5 Hz), 3.24 (2H, CH$_2$, t, J = 6.2 Hz), 4.13 (2H, CH$_2$O, t, J = 6.2 Hz), 7.41 (2H, 2xNH, brs), 7.51 (3H, CH-Aromatic, m), 7.93 (1H, NH, brs), 7.93 (2H, CH-Aromatic, m), 8.37 (1H, CH, s), 12.33 (1H, NH, brs) |

$^a$The solvent is MeOD.

Example 6

Enzyme Inhibitor Activites

The synthesized 2,4-diamino-6-ethylpyrimdine derivatives as the hydrochloride salts were tested for the activities against *Plasmodium falciparum* (*P. falciparum*) according to the standard methods. These include the inhibition of dihydrofolate reductase (DHFR) enzymes of *P. falciparum* including, wild type (WT) and quadruple mutants (N51IC59RS108NI164L) (QM). The inhibition was expressed as inhibition constants ($K_i$) in nano molar (nM). The selectivity for *P. falciparum* was tested by comparing with Human dihydrofolate reductase (hDHFR), which was expressed in term of selectivity ratio (the ratio between $K_i$ of hDHFR and pfDHFR) as shown in Table 3.

The inhibition constant ($K_i$) of the derivative compounds against the wild type and quadruple mutants enzymes of dihydrofolate reductase (DHFR) of *Plasmodium falciparum* (pfDHFR) are summarized in Table 3 below. The new pyrimidine derivatives showed low values of $K_i$ compared to pyrimethamine, which indicates that these compounds can inhibit both wild type and quadruple mutant pfDHFR better than pyrimethamine.

TABLE 3

Inhibition Constants ($K_i$) of 2,4-diamino-6-ethylpyrimidine derivatives for binding with wild type, quadruple mutants pfDHFR and human dihydrofolate reductase

| | $K_i$ pfDHFR (nM) | | | |
|---|---|---|---|---|
| Compound | WT | N51I + C59R + S108N + I164L (QM) | hDHFR | Selectivity ratio of $K_i$ hDHFR/$K_i$ QM |
| Pyrimethamine | 0.60 ± 0.20 | 385.00 ± 163.0 | 28.30 ± 2.50 | 0.07 |
| P218 | 0.43 ± 0.07 | 0.54 ± 0.12 | 17.4 ± 3.80 | 32.20 |
| 1 | 49.74 ± 4.18 | 6016.28 ± 772.30 | High | ND |
| 2 | 1034.53 ± 89.32 | 6649.42 ± 408.90 | >100000 | 15.03 |
| 3 | 11.35 ± 0.81 | 13.94 ± 1.98 | 3138.33 ± 242.17 | 225.13 |
| 4 | 3.30 ± 0.36 | 5.20 ± 0.62 | 555.42 ± 20.10 | 106.74 |
| 5 | 6.31 ± 0.40 | 7.61 ± 0.66 | 196.03 ± 20.67 | 25.75 |
| 6 | 10.34 ± 1.69 | 17.50 ± 2.19 | High | ND |
| 7 | 2.24 ± 0.10 | 70.14 ± 6.92 | 3222.47 ± 86.21 | 45.94 |
| 8 | 2.82 ± 0.10 | 49.75 ± 1.89 | 3681.93 ± 480.01 | 74.02 |
| 9 | 1.14 ± 0.06 | 10.75 ± 1.02 | 1670.53 ± 59.55 | 155.40 |
| 10 | 1.01 ± 0.04 | 6.96 ± 1.12 | High | ND |
| 11 | 1.12 ± 0.08 | 32.08 ± 8.31 | 1117.78 ± 91.43 | 34.84 |
| 12 | 0.82 ± 0.06 | 33.97 ± 5.51 | 874.56 ± 27.86 | 25.75 |

TABLE 3-continued

Inhibition Constants ($K_i$) of 2,4-diamino-6-ethylpyrimidine derivatives for binding with wild type, quadruple mutants pfDHFR and human dihydrofolate reductase

| | $K_i$ pfDHFR (nM) | | | |
|---|---|---|---|---|
| Compound | WT | N51I + C59R + S108N + I164L (QM) | hDHFR | Selectivity ratio of $K_i$ hDHFR/$K_i$ QM |
| 13 | 3.27 ± 0.28 | 377.48 ± 20.48 | High | ND |
| 14 | 8.62 ± 1.15 | 237.09 ± 41.74 | >500000 | >2108.90 |
| 15 | 1.85 ± 0.36 | 207.55 ± 16.62 | High | ND |
| 16 | 0.27 ± 0.03 | 6.18 ± 0.60 | 817.23 ± 145.14 | 132.21 |
| 17 | 42.73 ± 0.99 | 1992.20 ± 318.04 | >500000 | >250.97 |
| 18 | 6.54 ± 1.25 | 833.16 ± 44.98 | High | ND |
| 19 | 7.79 ± 1.33 | 671.27 ± 27.18 | High | ND |
| 20 | 0.39 ± 0.06 | 1.73 ± 0.18 | 80.21 ± 3.28 | 46.43 |
| 21 | 0.48 ± 0.10 | 8.56 ± 1.46 | 1059.02 ± 89.48 | 123.66 |
| 22 | 0.26 ± 0.04 | 4.64 ± 0.60 | High | ND |
| 23 | 0.25 ± 0.02 | 0.42 ± 0.06 | 22.69 ± 2.76 | 54.02 |
| 24 | 0.15 ± 0.02 | 1.90 ± 0.08 | 18.98 ± 1.92 | 9.98 |
| 25 | 0.35 ± 0.04 | 3.52 ± 0.73 | 44.82 ± 1.92 | 12.73 |
| 26 | 19.50 ± 1.06 | 387.63 ± 26.21 | High | ND |
| 27 | 9.41 ± 0.85 | 285.09 ± 14.06 | High | ND |
| 28 | 53.67 ± 5.60 | High | High | ND |
| 29 | 14.54 ± 1.62 | 476.77 ± 32.30 | High | ND |
| 30 | 8.86 ± 0.80 | 755.88 ± 62.59 | High | ND |
| 31 | 0.60 ± 0.01 | 9.71 ± 0.87 | 94.49 ± 5.58 | 9.73 |
| 32 | 0.36 ± 0.02 | 4.72 ± 0.77 | 54.35 ± 1.05 | 11.52 |
| 33 | 0.51 ± 0.08 | 38.07 ± 6.27 | 1481.74 ± 68.89 | 38.93 |
| 34 | 1.01 ± 0.05 | 77.60 ± 14.75 | 1078.03 ± 93.67 | 13.89 |
| 35 | 0.95 ± 0.02 | 65.03 ± 11.93 | 1170.45 ± 129.52 | 18.00 |
| 36 | 1.03 ± 0.20 | 64.60 ± 1.16 | 1346.68 ± 104.44 | 20.85 |
| 37 | 2.12 ± 0.18 | 106.06 ± 17.27 | >100000 | >942.86 |
| 38 | 0.55 ± 0.10 | 22.78 ± 3.09 | 1077.90 ± 30.95 | 47.32 |
| 39 | 1.33 ± 0.17 | 49.01 ± 6.73 | >100000 | >2040.39 |
| 40 | 1.28 ± 0.13 | 2.12 ± 0.17 | 279.29 ± 24.74 | 131.89 |
| 41 | 4.29 ± 0.31 | 316.29 ± 62.29 | >100000 | >316.16 |
| 42 | 1.15 ± 0.18 | 64.44 ± 7.59 | 1657.00 ± 76.67 | 25.71 |
| 43 | 4.02 ± 0.57 | 306.26 ± 36.48 | >100000 | >326.51 |
| 44 | 3.75 ± 0.31 | 244.97 ± 34.57 | >100000 | >408.21 |
| 45 | 1.99 ± 0.43 | 3.90 ± 0.68 | 37.00 ± 5.36 | 9.50 |
| 46 | 0.39 ± 0.03 | 1.74 ± 0.14 | 26.12 ± 0.24 | 15.01 |
| 47 | 0.27 ± 0.03 | 1.02 ± 0.07 | 21.45 ± 0.91 | 21.03 |
| 48 | 0.26 ± 0.07 | 0.87 ± 0.15 | 25.19 ± 8.90 | 28.95 |
| 49 | 0.19 ± 0.02 | 0.29 ± 0.01 | 12.64 ± 1.43 | 43.59 |
| 50 | 1.33 ± 0.07 | 55.61 ± 8.79 | 292.23 ± 22.19 | 5.25 |
| 51 | 0.44 ± 0.05 | 47.98 ± 1.54 | 256.29 ± 9.25 | 5.34 |
| 52 | 2.63 ± 0.26 | 93.16 ± 24.98 | >100000 | >1073.42 |
| 53 | 0.83 ± 0.08 | 45.53 ± 5.02 | 681.16 ± 70.33 | 14.96 |
| 54 | 1.19 ± 0.15 | 260.70 ± 19.02 | 540.31 ± 25.21 | 2.07 |
| 55 | 1.14 ± 0.17 | 32.86 ± 4.13 | >100000 | >3043.21 |
| 56 | 0.81 ± 0.07 | 46.74 ± 4.68 | >100000 | >2139.49 |
| 57 | 0.84 ± 0.08 | 77.99 ± 6.44 | 715.80 ± 78.27 | 9.18 |
| 58 | 0.55 ± 0.02 | 4.63 ± 0.22 | 20.40 ± 2.10 | 4.41 |
| 59 | 0.26 ± 0.01 | 1.56 ± 0.07 | 17.39 ± 1.14 | 11.15 |
| 60 | 1.02 ± 0.14 | 38.85 ± 5.58 | 275.71 ± 16.71 | 7.10 |
| 61 | 0.34 ± 0.05 | 37.73 ± 3.04 | 131.49 ± 0.88 | 3.49 |
| 62 | 0.74 ± 0.07 | 53.18 ± 8.93 | 133.54 ± 7.24 | 2.51 |
| 63 | 0.75 ± 0.10 | 33.95 ± 1.85 | 118.15 ± 14.78 | 3.48 |
| 64 | 0.60 ± 0.04 | 41.34 ± 7.41 | 183.78 ± 21.36 | 4.45 |
| 65 | 0.51 ± 0.04 | 56.66 ± 5.79 | 195.18 ± 8.20 | 3.44 |
| 66 | 0.86 ± 0.10 | 36.70 ± 4.79 | 102.46 ± 5.26 | 2.79 |
| 67 | 0.81 ± 0.05 | 27.34 ± 1.45 | >100000 | >3657.64 |
| 68 | 0.46 ± 0.06 | 16.04 ± 1.27 | 185.54 ± 4.66 | 11.57 |
| 69 | 0.90 ± 0.18 | 45.60 ± 4.68 | 318.36 ± 29.65 | 6.98 |
| 70 | 0.74 ± 0.09 | 30.24 ± 1.59 | 286.12 ± 47.11 | 9.46 |
| 71 | 0.76 ± 0.15 | 24.28 ± 1.75 | 202.88 ± 27.17 | 8.36 |
| 72 | 0.80 ± 0.09 | 30.25 ± 5.63 | 140.15 ± 21.99 | 4.63 |
| 73 | 0.65 ± 0.14 | 28.91 ± 2.56 | 357.34 ± 34.40 | 12.36 |
| 74 | 0.65 ± 0.06 | 33.99 ± 5.42 | 446.81 ± 110.21 | 13.15 |
| 75 | 0.69 ± 0.12 | 39.16 ± 3.82 | 301.35 ± 24.43 | 7.69 |
| 76 | 0.94 ± 0.16 | 7.28 ± 0.69 | 20.96 ± 1.24 | 2.88 |

Example 7

In Vitro Antimalarial Activites Against *P. falciparum* and Cytotoxicity Towards Mammalian Cells (Vero Cells)

The in vitro anti-malarial activity ($IC_{50}$ values) in micro molar (μM) of the pyrimidine derivatives against both wild-type (TM4/8.2) and quadruple mutant (V1/S) *P. falciparum* are shown in Table 4. The $IC_{50}$ of most compounds are lower than pyrimethamine indicating that they are more effective against *P. falciparum* for both wild-type and mutant strains than pyrimethamine. In addition, these compounds showed a good selectivity for *P. falciparum* and exhibited lower cytotoxicity in mammalian cells. Therefore these compounds have potentials to be developed into antimalarial drugs that are effective against drug-resistant malaria, showed good selectivity and low toxicity.

TABLE 4

Anti-plasmodial activities ($IC_{50}$) of 2,4-diamino-6-ethylpyrimidine derivatives against *P. falciparum* carrying various DHFR types: TM4/8.2 (wild type) and V1/S (N51I + C59R + S108 + I164L) and Cytotoxicity of 2,4-diamino-6-ethylpyrimidine derivatives in mammalian cells.

| Compound | $IC_{50}$ *P. falciparum* Strains (μM) | | Cytotoxicity against Vero cells ($IC_{50}$ (μM)) | Selectivity ratio ($IC_{50}$ ratio) Vero/V1/S |
|---|---|---|---|---|
| | TM4/8.2 (WT) | V1/S | | |
| Pyrimethamine | 0.058 ± 0.03 | >100 | >10 | >0.10 |
| P218 | 0.0046 ± 0.0019 | 0.056 ± 0.020 | >10 | >178.57 |
| 1 | >50 | >50 | >50 | — |
| 2 | >10 | >10 | >10 | — |
| 3 | 3.57 ± 1.25 | 19.90 ± 7.03 | >50 | >2.51 |
| 4 | 5.53 ± 0.84 | >25 | >25 | — |
| 5 | 7.95 ± 1.38 | >10 | >10 | — |
| 6 | 5.59 ± 1.54 | 4.31 ± 0.93 | >25 | >5.80 |
| 7 | 2.62 ± 0.33 | >50 | >50 | — |
| 8 | 5.58 ± 0.67 | 32.30 ± 3.06 | >50 | >1.55 |
| 9 | 2.24 ± 0.60 | 15.9 ± 5.63 | 47.40 ± 11.60 | 2.98 |
| 10 | 0.88 ± 0.36 | 21.00 ± 4.49 | 38.90 ± 2.14 | 1.85 |
| 11 | 2.42 ± 0.55 | >50 | 48.70 ± 13.57 | <0.97 |
| 12 | 0.97 ± 0.40 | >50 | 47.60 ± 6.27 | <0.95 |
| 13 | 5.73 ± 0.35 | >25 | >25 | — |
| 14 | 3.42 ± 0.61 | 4.43 ± 1.13 | >50 | >11.29 |
| 15 | 0.73 ± 0.23 | 17.60 ± 1.50 | >50 | >2.84 |
| 16 | 0.60 ± 0.24 | >25 | >25 | — |
| 17 | 4.25 ± 1.37 | 14.90 ± 3.82 | >50 | >3.35 |
| 18 | 10.50 ± 3.10 | 13.60 ± 3.22 | >50 | >3.68 |
| 19 | >10 | >10 | >10 | — |
| 20 | 0.67 ± 0.34 | 1.74 ± 0.51 | >25 | >14.37 |
| 21 | 0.49 ± 0.07 | >25 | >25 | — |
| 22 | 0.62 ± 0.18 | >50 | >50 | — |
| 23 | 0.0064 ± 0.0005 | 0.32 ± 0.12 | >25 | >78.13 |
| 24 | 0.055 ± 0.006 | >2 | >2 | — |
| 25 | 0.036 ± 0.010 | 4.65 ± 0.12 | 6.40 ± 1.08 | 1.38 |
| 26 | >25 | >25 | >25 | — |
| 27 | 16.10 ± 6.02 | >50 | >50 | — |
| 28 | >1[a] | >1[a] | >1[a] | — |
| 29 | >25 | >25 | >25 | — |
| 30 | 12.40 ± 4.71 | >50 | >50 | — |
| 31 | 1.80 ± 0.63 | >25 | >25 | — |
| 32 | 0.087 ± 0.03 | 3.75 ± 0.43 | >50 | >13.33 |
| 33 | 0.67 ± 0.13 | 15.70 ± 4.48 | >25 | >1.59 |
| 34 | 1.60 ± 0.79 | 18.90 ± 4.44 | >25 | >1.32 |
| 35 | 2.50 ± 0.34 | 20.90 ± 4.08 | >25 | >1.20 |
| 36 | 2.86 ± 0.56 | 17.50 ± 2.96 | >25 | >1.43 |
| 37 | 3.26 ± 0.81 | 20.20 ± 1.37 | 37.10 ± 1.81[b] | 1.83 |
| 38 | 0.57 ± 0.19 | >25 | >25 | — |
| 39 | 1.16 ± 0.55 | 9.08 ± 1.05 | >50 | >5.51 |
| 40 | 0.28 ± 0.13 | 3.38 ± 1.06 | >50 | >14.79 |
| 41 | 6.78 ± 2.21 | >10 | >10 | — |
| 42 | 1.19 ± 0.36 | >25 | >25 | — |
| 43 | 33.20 ± 14.20 | >50 | >50 | — |
| 44 | 7.77 ± 1.47 | >10 | >10 | — |
| 45 | 0.27 ± 0.08 | 6.37 ± 1.97 | >50 | >7.85 |
| 46 | 0.13 ± 0.04 | 17.70 ± 4.74 | 10.5 | 0.59 |
| 47 | 0.040 ± 0.007 | 5.51 ± 0.47 | 0.56 | 0.10 |
| 48 | 0.045 ± 0.0015 | 0.10 ± 0.03 | 0.76 | 7.60 |
| 49 | 0.007 ± 0.0015 | 0.13 ± 0.04 | >100 | >1052.63 |
| 50 | 2.25 ± 0.71 | 13.70 ± 4.08 | >50 | >3.65 |
| 51 | 0.83 ± 0.05 | 21.90 ± 5.88 | 75.90 ± 11.00 | 3.47 |
| 52 | 2.66 ± 0.31 | 15.10 ± 1.49 | >50 | >3.31 |
| 53 | 1.76 ± 0.67 | >10 | >10 | — |
| 54 | 3.82 ± 0.21 | >50 | >50 | — |
| 55 | 0.87 ± 0.11 | >25 | >25 | — |
| 56 | 0.58 ± 0.22 | 23.30 ± 2.47 | >100 | >4.29 |
| 57 | 0.73 ± 0.17 | >50 | >50 | — |

TABLE 4-continued

Anti-plasmodial activities (IC$_{50}$) of 2,4-diamino-6-ethylpyrimidine derivatives against *P. falciparum* carrying various DHFR types: TM4/8.2 (wild type) and V1/S (N51I + C59R + S108 + I164L) and Cytotoxicity of 2,4-diamino-6-ethylpyrimidine derivatives in mammalian cells.

| Compound | IC$_{50}$ *P. falciparum* Strains (µM) | | Cytotoxicity against Vero cells (IC$_{50}$ (µM)) | Selectivity ratio (IC$_{50}$ ratio) Vero/V1/S |
|---|---|---|---|---|
| | TM4/8.2 (WT) | V1/S | | |
| 58 | 0.048 ± 0.021 | 53.10 ± 15.20 | 5.59 ± 1.84 | 0.11 |
| 59 | 0.052 ± 0.010 | >10 | >10 | — |
| 60 | 1.20 ± 0.38 | 20.80 ± 1.86 | >50 | >2.40 |
| 61 | 0.84 ± 0.10 | 18.00 ± 7.77 | 31.30 ± 7.75 | 1.74 |
| 62 | 0.46 ± 0.07 | 3.98 ± 0.52 | 17.90 ± 6.23 | 4.50 |
| 63 | 0.40 ± 0.07 | >50 | >50 | — |
| 64 | 0.55 ± 0.12 | >50 | >50 | — |
| 65 | 0.40 ± 0.08 | >50 | >50 | — |
| 66 | 2.17 ± 0.54 | >10 | >10 | — |
| 67 | 1.02 ± 0.53 | 19.00 ± 6.70 | 28.90 ± 5.74 | 1.52 |
| 68 | 0.45 ± 0.09 | 12.90 ± 5.71 | 43.50 ± 13.40 | 3.37 |
| 69 | 0.79 ± 0.38 | >25 | >25 | — |
| 70 | 1.18 ± 0.03 | 24.30 ± 9.37 | 63.50 ± 17.60 | 2.61 |
| 71 | 1.09 ± 0.44 | 18.70 ± 1.90 | >25 | >1.34 |
| 72 | 0.23 ± 0.03 | >50 | >50 | — |
| 73 | 0.041 ± 0.006 | >50 | >50 | — |
| 74 | 0.40 ± 0.13 | 15.90 ± 2.11 | >50 | >3.15 |
| 75 | 2.65 ± 0.43 | >50 | >50 | — |
| 76 | 0.011 ± 0.002 | 17.80 ± 6.80 | 1.33 ± 0.46 | 0.075 |

$^a$maximum concentration tested was 1 µM due to poor solubility,
$^b$preliminary data.

The invention claimed is:

1. Derivatives of 2,4-diamino-6-ethylpyrimidine of Formula (I):

(I)

Wherein X1, X2 are oxygen or absent, Y1, Y2 are (CH2)1-3alkyl or absent, Z is (1-substituted-1H-1,2,3-triazol-4-yl) ring, (3-(substituted(isoxazol-5-yl) ring, (2-(substituted(oxazol-4-yl) ring, (2-(substituted)thiazol-4-yl) ring; wherein Ar is an aromatic ring or substituted aromatic ring as below:
a. Z is a ring of (1-substituted-1H-1,2,3-triazol-4-yl); Ar is phenyl or carboxyl substituted phenyl; no group X1, X2, Y1 and Y2
b. Z is a ring of (1-substituted-1H-1,2,3-triazol-4-yl); Ar is phenyl, carboxymethyl substituted phenyl, carboxyl-substituted phenyl or diphenylcarbamoyl substituted phenyl; Y2 is C1-3 alkyl; no group X1, X2 and Y1
c. Z is a ring of (1-substituted-1H-1,2,3-triazol-4-yl); Ar is chloro-substituted phenyl or carboxymethyl-substituted phenyl; X2 is oxygen; Y2 is C2-3 alkyl; no group X1 and Y1
d. Z is a ring of (3-(substituted)isoxazol-5-yl); Ar is phenyl, fluoro-substituted phenyl, chloro-substituted phenyl, bromo-substituted phenyl, trifluoromethyl-substituted phenyl, methoxy-substituted phenyl, nitro-substituted phenyl, cyano substituted phenyl, carboxymethyl-substituted phenyl or carboxyl-substituted phenyl; X1 is oxygen; Y1 is C1-3 alkyl; no group X2 and Y2
e. Z is a ring of (2-(substituted)oxazol-4-yl); Ar is phenyl, chloro-substituted phenyl, methyl-substituted phenyl, nitro-substituted phenyl, alkoxy carbonylmethoxy substituted phenyl, carboxymethoxy-substituted phenyl, alkoxy carbonyl-substituted phenyl or carboxy-substituted phenyl; X1 is oxygen; Y1 is C1-2 alkyl; no group X2 and Y2
f. Z is a ring of (2-(substituted)thiazol-4-yl); Ar is phenyl, fluoro-substituted phenyl, chloro-substituted phenyl, bromo-substituted phenyl, methyl-substituted phenyl, m ethoxy-substituted phenyl, nitro-substituted phenyl, alkoxy carbonylmethoxy substituted phenyl, carboxymethoxy-substituted phenyl, alkoxy carbonyl-substituted phenyl or carboxyl-substituted phenyl; X1 is oxygen; Y1 is C1-2 alkyl; no group X2 and Y2.

2. Formulations of compounds of Formula (I) for inhibition of *Plasmodium falciparum* comprise of one or more compounds according to claim 1 or their salts and pharmaceutically acceptable excipients.

3. Formulations of compounds of Formula (I) for inhibition of *Plasmodium falciparum* according to claim 2, wherein the said salt is hydrochloride salt.

4. The derivative compounds of 2,4-diamino-6-ethylpyrimidine of claim 1, wherein said compounds are compound 1 to compound 56 below:
(1) 2,4-diamino-6-ethyl-5-(1-phenyl-1H-1,2,3-triazol-4-yl)pyrimidine
(2) 2,4-diamino-6-ethyl-5-(1-(3-(carboxy)phenyl)-1H-1,2,3-triazol-4-yl)pyrimidine
(3) 2,4-diamino-6-ethyl-5-(1-benzyl-1H-1,2,3-triazol-4-yl)pyrimidine
(4) 2,4-diamino-6-ethyl-5-(1-((4-(carboxymethyl)phenyl)methyl)-1H-1,2,3-triazol-4-yl)pyrimidine
(5) 2,4-diamino-6-ethyl-5-(1-((4-(carboxy)phenyl)methyl)-1H-1,2,3-triazol-4-yl)pyrimidine
(6) 2,4-diamino-6-ethyl-5-(1-((4-(diphenylcarbamoyl)phenyl)methyl)-1H-1,2,3-triazol-4-yl)pyrimidine (7) 2,4-diamino-6-ethyl-5-(1-(phenylethyl)-1H-1,2,3-triazol-4-yl)pyrimidine
(8) 2,4-diamino-6-ethyl-5-(1-(3-phenylpropyl)-1H-1,2,3-triazol-4-yl)pyrimidine
(9) 2,4-diamino-6-ethyl-5-(1-(2-(4-(chloro)phenoxy)ethyl)-1H-1,2,3-triazol-4-yl)pyrimidine
(10) 2,4-diamino-6-ethyl-5-(1-(2-(4-(carboxymethyl)phenoxy)ethyl)-1H-1,2,3-triazol-4-yl)pyrimidine
(11) 2,4-diamino-6-ethyl-5-(1-(3-(4-(chloro)phenoxy)propyl)-1H-1,2,3-triazol-4-yl)pyrimidine
(12) 2,4-diamino-6-ethyl-5-(1-(3-(4-(carboxymethyl)phenoxy)propyl)-1H-1,2,3-triazol-4-yl)pyrimidine
(13) 2,4-diamino-6-ethyl-5-((3-(phenyl)isoxazol-5-yl)methoxy)pyrimidine
(14) 2,4-diamino-6-ethyl-5-((3-(4-(fluoro)phenyl)isoxazol-5-yl)methoxy)pyrimidine
(15) 2,4-diamino-6-ethyl-5-((3-(4-(chloro)phenyl)isoxazol-5-yl)methoxy)pyrimidine
(16) 2,4-diamino-6-ethyl-5-((3-(4-(bromo)phenyl)isoxazol-5-yl)methoxy)pyrimidine
(17) 2,4-diamino-6-ethyl-5-((3-(3-(trifluoromethyl)phenyl)isoxazol-5-yl)methoxy)pyrimidine
(18) 2,4-diamino-6-ethyl-5-((3-(3-(methoxy)phenyl)isoxazol-5-yl)methoxy)pyrimidine
(19) 2,4-diamino-6-ethyl-5-((3-(3-(nitro)phenyl)isoxazol-5-yl)methoxy)pyrimidine
(20) 2,4-diamino-6-ethyl-5-((3-(3-(carboxy)phenyl)isoxazol-5-yl)methoxy)pyrimidine
(21) 2,4-diamino-6-ethyl-5-((3-(4-(trifluoromethyl)phenyl)isoxazol-5-yl)methoxy)pyrimidine
(22) 2,4-diamino-6-ethyl-5-((3-(4-(methoxy)phenyl)isoxazol-5-yl)methoxy)pyrimidine
(23) 2,4-diamino-6-ethyl-5-((3-(4-(nitro)phenyl)isoxazol-5-yl)methoxy)pyrimidine
(24) 2,4-diamino-6-ethyl-5-((3-(4-(carboxy)phenyl)isoxazol-5-yl)methoxy)pyrimidine
(25) 2,4-diamino-6-ethyl-5-(3-(3-(4-(chloro)phenyl)isoxazol-5-yl)propoxy)pyrimidine
(26) 2,4-diamino-6-ethyl-5-(3-(3-(3-(trifluoromethyl)phenyl)isoxazol-5-yl)propoxy)pyrimidine
(27) 2,4-diamino-6-ethyl-5-(3-(3-(3-(cyano)phenyl)isoxazol-5-yl)propoxy)pyrimidine
(28) 2,4-diamino-6-ethyl-5-(3-(3-(3-(carboxymethyl)phenyl)isoxazol-5-yl)propoxy)pyrimidine
(29) 2,4-diamino-6-ethyl-5-(3-(3-(3-(carboxy)phenyl)isoxazol-5-yl)propoxy)pyrimidine
(30) 2,4-diamino-6-ethyl-5-((2-(phenyl)oxazol-4-yl)methoxy)pyrimidine
(31) 2,4-diamino-6-ethyl-5-((2-(3-(methyl)phenyl)oxazol-4-yl)methoxy)pyrimidine
(32) 2,4-diamino-6-ethyl-5-((2-(3-(nitro)phenyl)oxazol-4-yl)methoxy)pyrimidine
(34) 2,4-diamino-6-ethyl-5-((2-(3-(carboxymethoxy)phenyl)oxazol-4-yl)methoxy)pyrimidine
(35) 2,4-diamino-6-ethyl-5-((2-(4-(chloro)phenyl)oxazol-4-yl)methoxy)pyrimidine
(37) 2,4-diamino-6-ethyl-5-((2-(4-(carboxymethoxy)phenyl)oxazol-4-yl)methoxy)pyrimidine
(38) 2,4-diamino-6-ethyl-5-(2-(2-(phenyl)oxazol-4-yl)ethoxy)pyrimidine
(39) 2,4-diamino-6-ethyl-5-(2-(2-(4-(carboxy)phenyl)oxazol-4-yl)ethoxy)pyrimidine
(40) 2,4-diamino-6-ethyl-5-((2-(phenyl)thiazol-4-yl)methoxy)pyrimidine
(41) 2,4-diamino-6-ethyl-5-((2-(3-(methyl)phenyl)thiazol-4-yl)methoxy)pyrimidine
(42) 2,4-diamino-6-ethyl-5-((2-(3-(nitro)phenyl)thiazol-4-yl)methoxy)pyrimidine
(44) 2,4-diamino-6-ethyl-5-((2-(3-(carboxymethoxy)phenyl)thiazol-4-yl)methoxy)pyrimidine
(45) 2,4-diamino-6-ethyl-5-((2-(3-(carboxymethyl)phenyl)thiazol-4-yl)methoxy)pyrimidine
(46) 2,4-diamino-6-ethyl-5-((2-(3-(carboxy)phenyl)thiazol-4-yl)methoxy)pyrimidine
(47) 2,4-diamino-6-ethyl-5-((2-(4-(methyl)phenyl)thiazol-4-yl)methoxy)pyrimidine
(48) 2,4-diamino-6-ethyl-5-((2-(4-(methoxy)phenyl)thiazol-4-yl)methoxy)pyrimidine
(49) 2,4-diamino-6-ethyl-5-((2-(4-(fluoro)phenyl)thiazol-4-yl)methoxy)pyrimidine
(50) 2,4-diamino-6-ethyl-5-((2-(4-(chloro)phenyl)thiazol-4-yl)methoxy)pyrimidine
(51) 2,4-diamino-6-ethyl-5-((2-(4-(bromo)phenyl)thiazol-4-yl)methoxy)pyrimidine
(53) 2,4-diamino-6-ethyl-5-((2-(4-(carboxymethoxy)phenyl)thiazol-4-yl)methoxy)pyrimidine
(54) 2,4-diamino-6-ethyl-5-((2-(4-(carboxymethyl)phenyl)thiazol-4-yl)methoxy)pyrimidine
(55) 2,4-diamino-6-ethyl-5-((2-(4-(carboxy)phenyl)thiazol-4-yl)methoxy)pyrimidine
(56) 2,4-diamino-6-ethyl-5-(2-(2-(phenyl)thiazol-4-yl)ethoxy)pyrimidine.

\* \* \* \* \*